United States Patent
Yamada et al.

(10) Patent No.: US 10,694,998 B2
(45) Date of Patent: Jun. 30, 2020

(54) MOVING BODY INFORMATION DETECTION TERMINAL

(71) Applicant: ASIA AIR SURVEY CO., LTD., Tokyo (JP)

(72) Inventors: Takayuki Yamada, Tokyo (JP); Yuichi Fujimoto, Tokyo (JP); Toshihiko Koyama, Tokyo (JP); Yukihiro Minami, Tokyo (JP)

(73) Assignee: ASIA AIR SURVEY CO., LTD., Tokyo (JP)

(*) Notice: Subject to any disclaimer, the term of this patent is extended or adjusted under 35 U.S.C. 154(b) by 0 days.

(21) Appl. No.: 16/338,284

(22) PCT Filed: Sep. 29, 2017

(86) PCT No.: PCT/JP2017/035648
§ 371 (c)(1),
(2) Date: Mar. 29, 2019

(87) PCT Pub. No.: WO2018/062534
PCT Pub. Date: Apr. 5, 2018

(65) Prior Publication Data
US 2020/0029896 A1    Jan. 30, 2020

(30) Foreign Application Priority Data

Sep. 30, 2016 (JP) ................................. 2016-193860
Aug. 9, 2017 (JP) ................................. 2017-154125

(51) Int. Cl.
*A61B 5/00* (2006.01)
*G01S 19/01* (2010.01)
*H04W 4/80* (2018.01)

(52) U.S. Cl.
CPC ............ *A61B 5/681* (2013.01); *A61B 5/0022* (2013.01); *G01S 19/01* (2013.01); *H04W 4/80* (2018.02)

(58) Field of Classification Search
CPC ....... A61B 5/681; A61B 5/0022; G01S 19/01; H04W 4/80; A63B 24/0062; A63B 24/00
See application file for complete search history.

(56) References Cited

U.S. PATENT DOCUMENTS 6,806,814 B1 * 10/2004 Iverson .................... G08G 1/20
340/5.74
9,087,159 B2 * 7/2015 Oleson ............... A63B 24/0062
(Continued)

FOREIGN PATENT DOCUMENTS

| JP | 2008-272163 | 11/2008 |
|---|---|---|
| JP | 2011-158990 | 8/2011 |
| JP | 2014-117551 | 6/2014 |

OTHER PUBLICATIONS

Official Communication issued in International Bureau of WIPO Patent Application No. PCT/JP2017/035648, dated Dec. 12, 2017.

*Primary Examiner* — Joseph H Feild
*Assistant Examiner* — Rufus C Point
(74) *Attorney, Agent, or Firm* — Greenblum & Bernstein, P.L.C.

(57) ABSTRACT

A wearable device includes; a near field communication module; a position sensor module that extracts Raw data used for determining positional data, from GNSS data from GNSS satellites; an internal timer that outputs system time after output timing of positional data synchronized with the Raw data; sensor modules having various kinds of sensors that detect moving body information; a storage unit that stores therein detection data from the various kinds of sensors; a unit that stores the detection data from the various kinds of sensors in the storage unit for every given time; a (Continued)

unit that calculates positional data on the basis of the Raw data; aid a unit that creates moving body information so that the system time and the positional data are associated with detection data stored in a memory area, and transmits the moving body information to a display device.

11 Claims, 22 Drawing Sheets

(56) References Cited

U.S. PATENT DOCUMENTS

| | | | | |
|---|---|---|---|---|
| 2002/0071677 | A1* | 6/2002 | Sumanaweera | H04N 1/00127 396/429 |
| 2002/0186412 | A1* | 12/2002 | Murashita | H04N 1/00127 358/1.16 |
| 2003/0236893 | A1* | 12/2003 | Nakamura | G06F 9/4843 709/228 |
| 2005/0057344 | A1* | 3/2005 | Davis | G08G 1/205 340/425.5 |
| 2008/0043715 | A1* | 2/2008 | Ijiri | G01S 5/0027 370/350 |
| 2011/0260917 | A1* | 10/2011 | Street | G01S 19/14 342/357.75 |
| 2013/0132414 | A1* | 5/2013 | Hayato | G06F 16/58 707/758 |
| 2014/0143834 | A1* | 5/2014 | Stahlin | H04L 67/12 726/3 |
| 2014/0172132 | A1 | 6/2014 | Ura | |
| 2015/0256689 | A1* | 9/2015 | Erkkila | G11B 27/30 386/228 |
| 2018/0376307 | A1* | 12/2018 | Itatsu | H04W 4/46 |
| 2020/0023237 | A1* | 1/2020 | Yamada | H04M 11/00 |

* cited by examiner

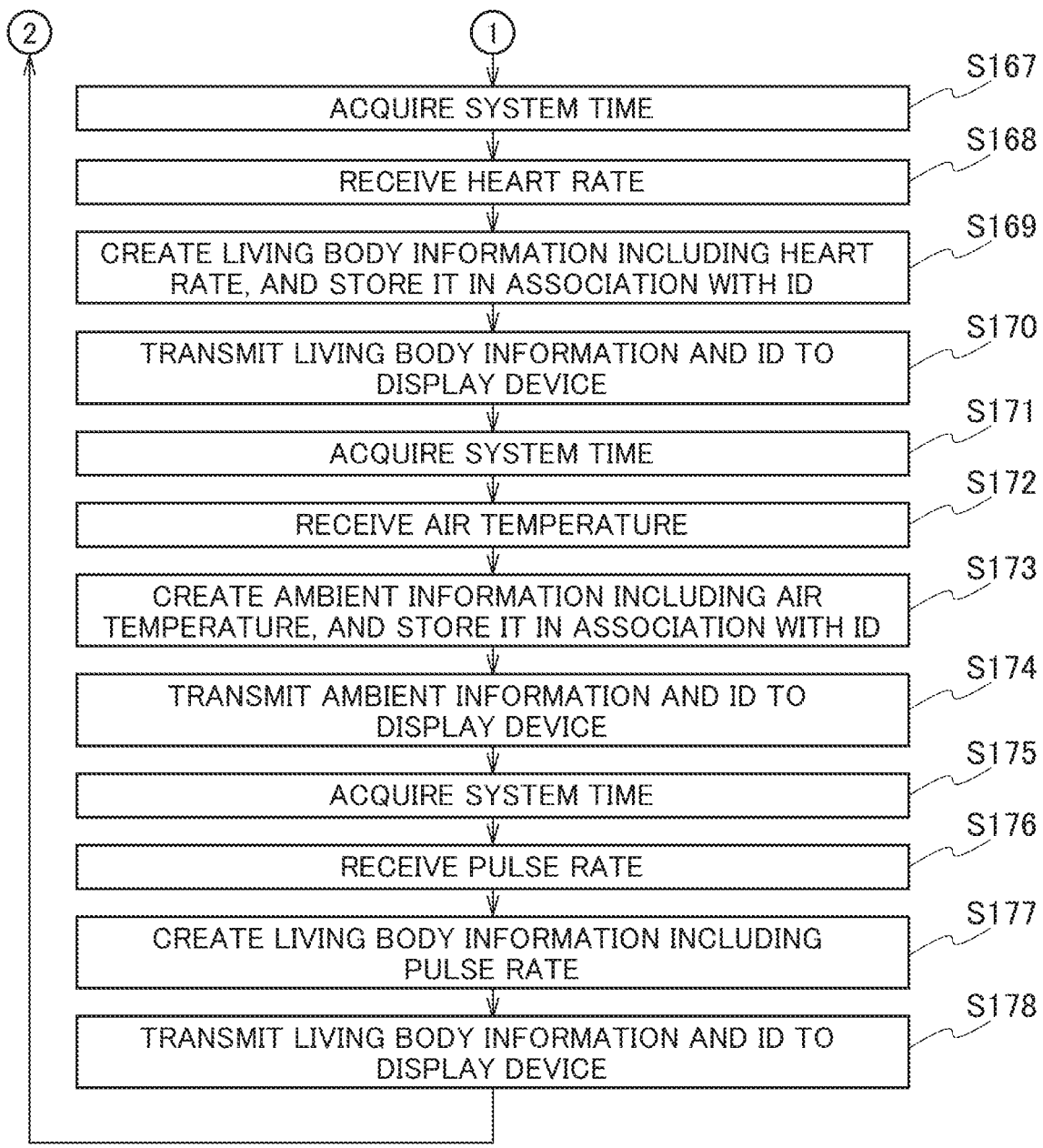

FIG. 10

SYSTEM TIME | POSITION DATA | SENSOR DATA

YYYY/MM/DD:HH:MM:01.100, Ei,Ni + HEART RATE + ID

FIG. 16(a)

| FOR POSITION | FOR TIME | | | | ... | |
|---|---|---|---|---|---|---|

{ FOR SENSOR DATA }

TRANSMISSION FORMAT KSRi

FIG. 16(b)

| DETECTION POSITION Pi IN UNITS OF 100 msec | SYSTEM TIME STi (ex. 100 msec) | FOR AIR PRESSURE | FOR ATTITUDE | FOR ACCEL-ERATION | FOR HEART RATE | FOR AIR TEMPER-ATURE | FOR PULSE RATE |
|---|---|---|---|---|---|---|---|

…

MOVING BODY INFORMATION DETECTION TERMINAL

TECHNICAL FIELD

The present invention relates to a moving body information detection terminal attached to a living body and suitable for use in the case of obtaining information about the living body.

BACKGROUND ART

Heretofore, there has been disclosed a technology regarding a living body information monitor system including: a living body information transmission terminal that is attached to a subject such as a dog and racehorse, acquires living body information of the subject, and transmits the acquired living body information; a living body information measuring device that receives the living body information transmitted from the living body information transmission terminal (refer to PTL 1).

Paragraphs [0050] to [0054] in PTL 1 regarding the living body information monitor system have disclosed that the living body information of the subject is detected, and in addition, a GPS reception unit is attached to the subject, and a current position and the living body information are accumulated in association with each other and are transmitted.

Moreover, paragraph [0059] discloses that a living body monitor instrument displays the living body information and position information in association with each other.

CITATION LIST

Patent Literature

PTL 1: JP 2008-272163 A

SUMMARY

Technical Problem

Generally, position information is detected by a GPS receiver at an interval of 1 sec. In contrast, a subject of which moving speed is fast moves by no less than several meters to several 10 meters for 1 sec.

However, the living body information transmission terminal of the living body information monitor system described in PTL 1 merely transmits the current position and the living body information in association with each other, and accordingly, can only transmit position information and living body information in association with each other at a time point when sec has elapsed.

That is, even if a position of the subject of which moving speed is fast is acquired and transmitted, the position is a position to which the subject has already moved by several meters to several 10 meters, and accordingly, there has been a problem that the living body information monitor system is unsuitable for detecting the position of the subject of which moving speed is fast.

Moreover, there are a variety of types in the living body information, and timings of acquiring such various types of the living body information also differ from one another. However, in PTL 1, the position information and the living body information at the time point when 1 sec has elapsed are only associated with each other, and accordingly, the various types of living body information cannot be associated with one another at the same time.

That is, the sensor for detecting the living body information, the sensor being for use in the living body information transmission terminal in PTL 1, has had a problem that a type thereof is restrictive.

Hence, the living body information transmission terminal of the living body information monitor system described in PTL 1 has had a problem that this living body information transmission terminal can only transmit living body information, which is detected by a fixed type of sensor, in association with the position information transmitted at the interval of 1 sec.

The present invention has been made in consideration of such circumstances as described above. It is an object of the present invention to obtain a moving body information detection terminal capable of detecting a precise position of a moving body even if the moving body moves at a fast moving speed, and capable of incorporating plural types of sensors therein and grasping association between outputs of such various sensors and the precise position.

Solution to Problem

In order to solve the above-described problem, a moving body information detection terminal according to the present invention is a moving body information detection terminal mounted on a moving body, including:
- a communication module;
- a position sensor module that receives global navigation satellite system (GNSS) data sent from a GNSS satellite and extracts, from the GNSS data, Raw data for obtaining position data;
- an internal tinier that outputs a system time no more than output timing of the position data synchronized with the Raw data;
- a moving body situation detection sensor module including a variety of sensors that detect various pieces of information regarding the moving body at intrinsic pieces of timing and output the detected pieces of information as moving body situation detection data;
- a storage region where the moving body situation detection data of the variety of sensors are stored;
- a unit that overwrites the moving body situation detection data to a predetermined memory region of the storage region every fixed time, the moving body situation detection data being sent from the variety of sensors;
- a unit that calculates the position data on the basis of the Raw data; and
- a unit that defines the system time and the position data as header information, creates moving body information so that the moving body situation detection data stored in the memory region at a present time point is associated with the header information, and causes the communication module to transmit the created moving body information to an external device.

Effect

In accordance with the present invention, the moving body situation detection information detected by the variety of sensors is sampled at the system time no more than the output interval of the Raw data that is original data of the GNSS position information. Accordingly, it is possible to incorporate the plurality of sensors different in acquisition timing, and the moving body situation detection information that is outputs of the variety of sensors can be acquired as much as possible at the same time as the system time.

Moreover, the acquired moving body situation detection information is transmitted to the external device in association with the system time and with the position information. Accordingly, even if the moving body moves fast, the external device can calculate an accurate position thereof, and this accurate position can be displayed in association with each piece of the moving body situation detection information.

Therefore, the external device can finely grasp where and how the moving body stands at the present time point.

For example, when the moving body is a soccer player, a user (a manager or a coach) of the external device can grasp under which situation and how the player moves at a certain spot in units of the detection position.

BRIEF DESCRIPTION OF DRAWINGS

FIGS. 9A and 9B show a flowchart at the time when the wearable device transmits the moving body information to the display device according to a modified example of the first embodiment;

FIG. 10 is a view illustrating an example of the moving body information according the modified example;

FIG. 16($a$) is a view illustrating an example of a transmission format created by an initial time capture format creation section of the wearable device, and FIG. 16($b$) is a view illustrating an example of format regions of the transmission format;

DESCRIPTION OF EMBODIMENTS

Hereinafter, a description will be given of embodiments of the present invention with reference to the drawings.

Note that the embodiments illustrated below exemplify a device and a method for embodying the technical idea (structure, disposition) of the invention, and the technical idea of the present invention is not limited to those described below. The technical idea of the present invention can be modified in various ways within the scope of the matters described in the scope of claims.

Particularly, it should be noted that the drawings are schematic and are different from actual ones in terms of device and system configuration and the like.

This embodiment is a moving body information detection terminal mounted on such a moving non-living body (a moving body) as a drone and a robot and a heavy machine such as an agricultural machine and a construction machine as well as on such a moving living body (a moving body) as a person and an animal. This embodiment is applied, for example, to such a case of acquiring a current situation of the moving body and transmitting the acquired current situation to a remote place in real time.

Hereinafter, a specific description will be given of the moving body information detection terminal, where the moving body is a living body. This moving body may be such an athlete as a marathon runner, a rugby player, a soccer player, a table tennis player, and a bicycle racer. The first embodiment will be described on the premise that the moving body is an athlete SPi of sports. That is, the moving body information detection terminal according to the first embodiment is an example of the case of being a wearable device that transmits moving body information in which position information of a high-sensitivity receiver (hereinafter, referred to as a "global navigation satellite system (GLASS)" module) is associated with such moving body living body information (simply referred to as living body information) as a heart rate, pulse rate and body temperature of the athlete SPi and with such moving body state information (simply referred to as state information) as an attitude value and acceleration of the athlete SPi. Moreover, such moving body ambient information (simply referred to as ambient information or environment information) as an air pressure and an air temperature (temperature) around the athlete SPi and a user ID for identifying the athlete SPi or a device ID for identifying the terminal mounted on the athlete SPi may be associated with the moving body information.

In the following description, in the first embodiment, an overview of the moving body information detection terminal will be described, and in second, third and fourth embodiments, specific examples (application examples) of the moving body information detection terminal will be described.

First Embodiment

<Overview of Moving Body Information Detection Terminal>

Figure 1:
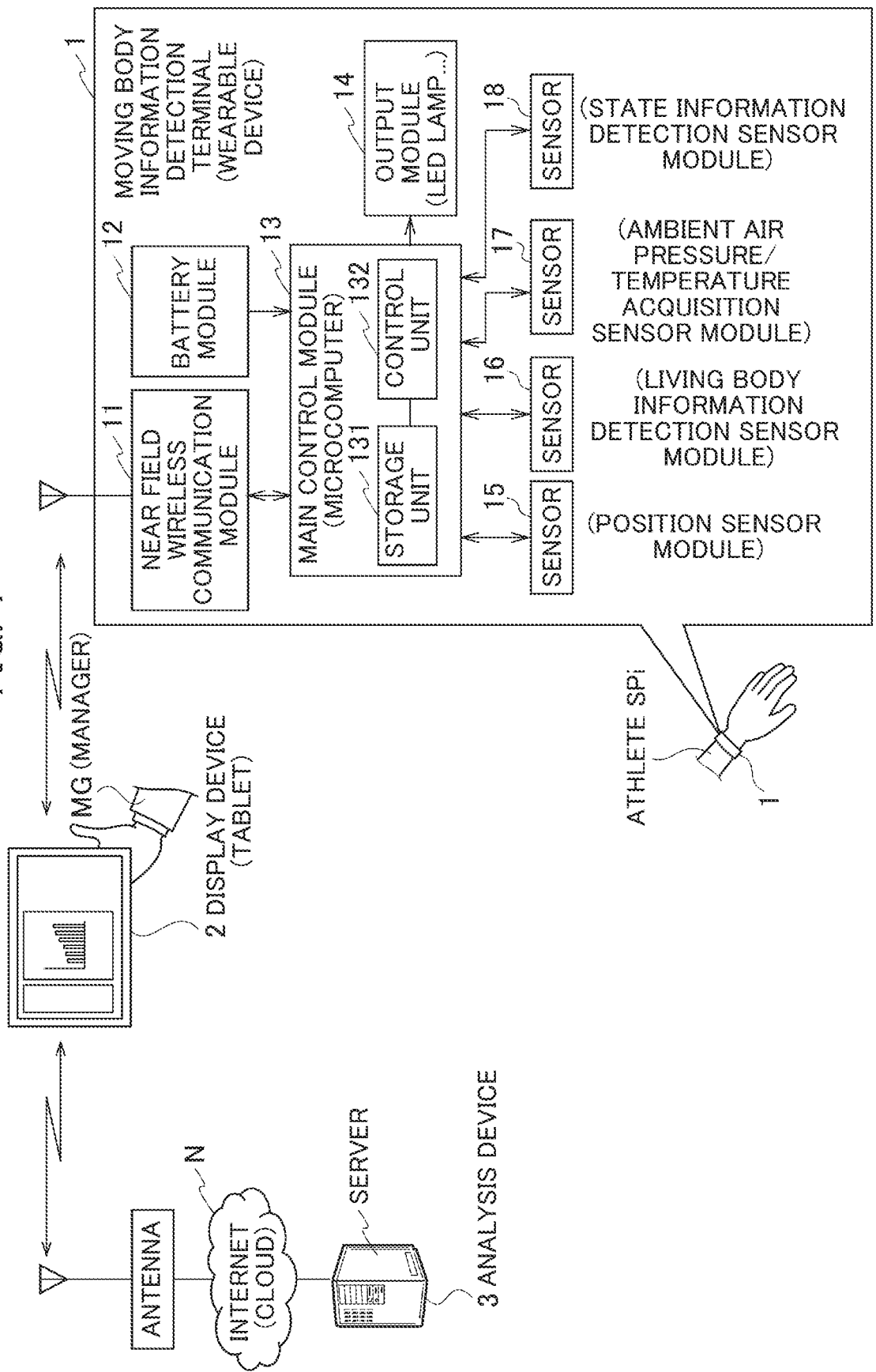
FIG. 1 is a diagram illustrating a schematic configuration of a moving body information detection terminal (a wearable device) according to a first embodiment.

FIG. 1 is a schematic configuration diagram for explaining the overview of the moving body information detection terminal (hereinafter, referred to as a "wearable device 1") according to the first embodiment. This wearable device 1 is, for example, a wristwatch-type wearable computer mounted on the wrist of the athlete SPi (a living body).

Moreover, in FIG. 1, as an example of external devices, a communication device (hereinafter, also referred to as a "display device") and an analysis device 3 connected to a cloud or the like on the Internet N will be exemplified and described. The display device is composed, for example, of a tablet terminal (simply also referred to as a "tablet 2").

Preferably; the tablet 2 is held, for example, by a manager MG of a team to which the athlete SPi belongs. The display device may be not only the tablet 2 but also a smart phone, a portable laptop computer (laptop PC) or the like.

Here, the wearable device 1 may be mounted by each of a plurality of the athletes SPi.

Figure 2:
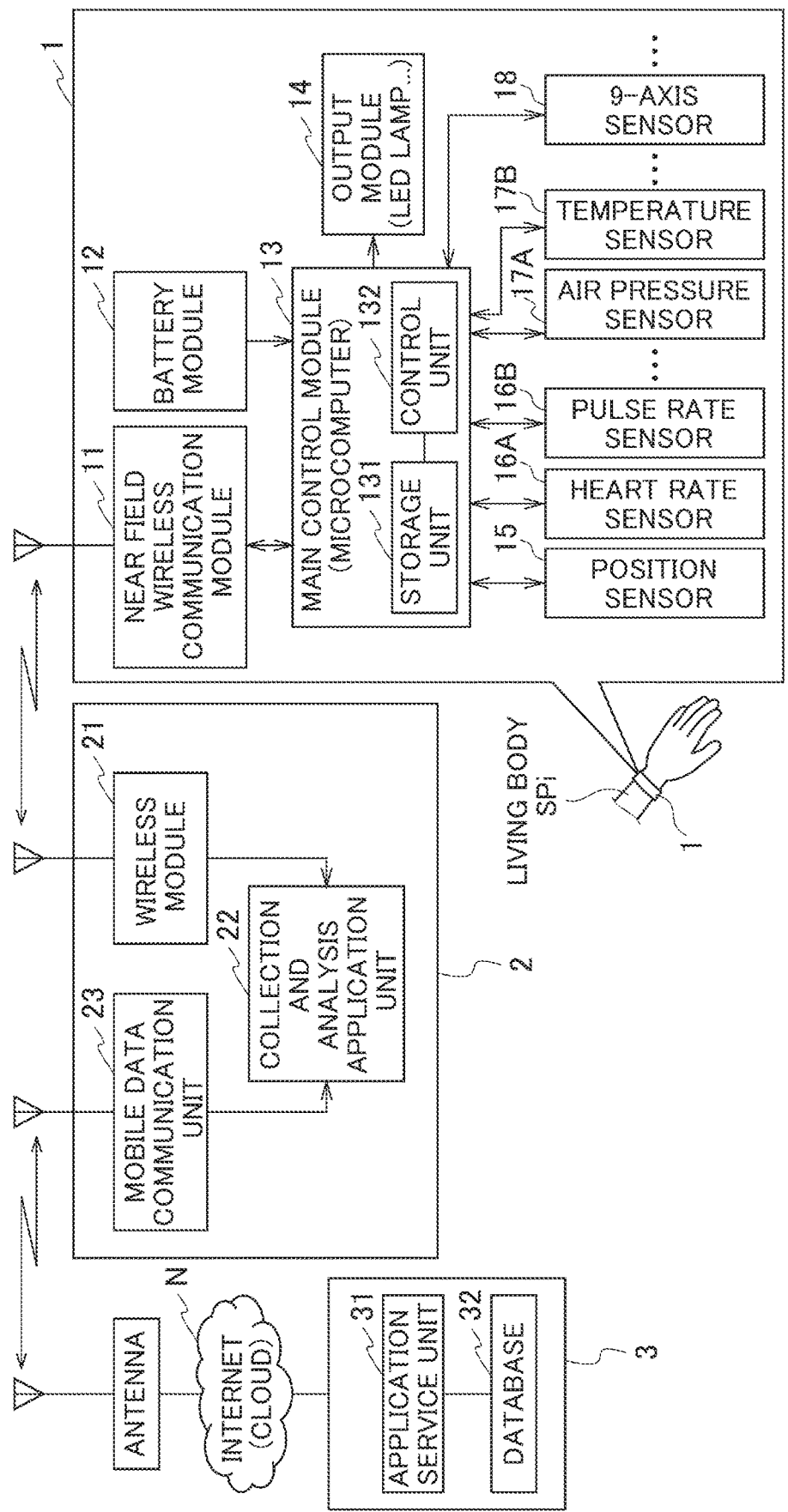
FIG. 2 is a diagram illustrated for explaining an overview of external devices (a display device and an analysis device) of the wearable device illustrated in FIG. 1.

As illustrated in FIG. 2, the wearable device 1 includes: a near field wireless communication module 11 (hereinafter, also referred to as a wireless module); a battery module 12; a main control module 13; an output module 14; and a plurality of moving body situation detection sensor modules.

The main control module 13 is, for example, a single board computer (also referred to as a microcontroller) that mounts a processor thereon, and includes a storage unit 131, a control unit 132, an interface illustrated) that connects both to each other.

Moreover, the plurality of moving body situation detection sensor modules are composed of: a position sensor module 15 (referred to as a high-sensitivity position detection module or a GNSS module); a living body information detection sensor module 16; an ambient information acquisition sensor module 17 that acquires environment information (ambient information) such as an air pressure and an air temperature around the athlete SPi; a state information detection sensor module 18 for detecting an attitude and speed of the athlete SPi; and the like.

For example, the position sensor module 15 is a satellite positioning system module such as a global positioning system (GPS) that performs positioning using an artificial satellite to be described later. The position sensor module 15 may be, for example, a module that receives GNSS data sent from a GNSS satellite and extracts Raw data for obtaining position data.

The living body information detection sensor module 16 is a heart rate sensor 16A, a pulse rate sensor 16B and the like which acquire living body information (moving body living body information) such as a heart rate and pulse rate of the athlete SPi. The ambient information acquisition sensor module 17 is an air pressure sensor 17A, an air temperature sensor 17B and the like which acquire ambient information (moving body ambient information) such as an air pressure and air temperature of a sports arena. The state information detection sensor module 18 is, for example, a 9-axis sensor including a gyro sensor (3 axes), an acceleration sensor (3 axes) and a geomagnetic sensor (3 axes), which acquire state information (moving body state information) such as an attitude value and acceleration of the athlete SPi.

The output module 14 is composed, for example, of an LED lamp, a vibrator, a voice reproduction device (a speaker or a buzzer) and the like. The battery module 12 is composed by including a battery.

<Overview of Communication Device>

Next, a configuration of the tablet 2 will be briefly described.

The tablet 2 illustrated in FIG. 2 includes a wireless module 21, a collection and analysis application unit 22, a mobile data communication unit 23 and the like.

This tablet 2 is used by the manager MG who desires to grasp a relationship between a position and degree of tiredness of the athlete SPi, for example, during a game or an exercise.

By the mobile data communication unit 23, the tablet 2 is connectable to the Internet N through an antenna installed by a communication provider. Meanwhile, the analysis device 3 is also connectable to the Internet N. In this way, the tablet 2 and the analysis device 3 are communicable with each other.

<Overview of Analysis Device>

Next, a configuration of the analysis device 3 will be briefly described.

As illustrated in FIG. 2, the analysis device 3 includes: includes: an application service unit 31 that is in charge of performance measurement, sensor correction, social networking service (SNS), human resource matching, medical treatment, training and the like for the athlete SPi; and a database 32 that stores personal data such as a biography and physical ability of the athlete SPi, team data, environment data analysis data and the like.

This analysis device 3 may be a device for use by the manager MG who desires to grasp a condition and the like of the athlete SPi in a manager room, a staff room and the like, for example, before a game.

Here, pre-registration of identification information of the wearable device I will be described.

(Pre-registration of Identification Information of Wearable Device 1)

Figure 3:
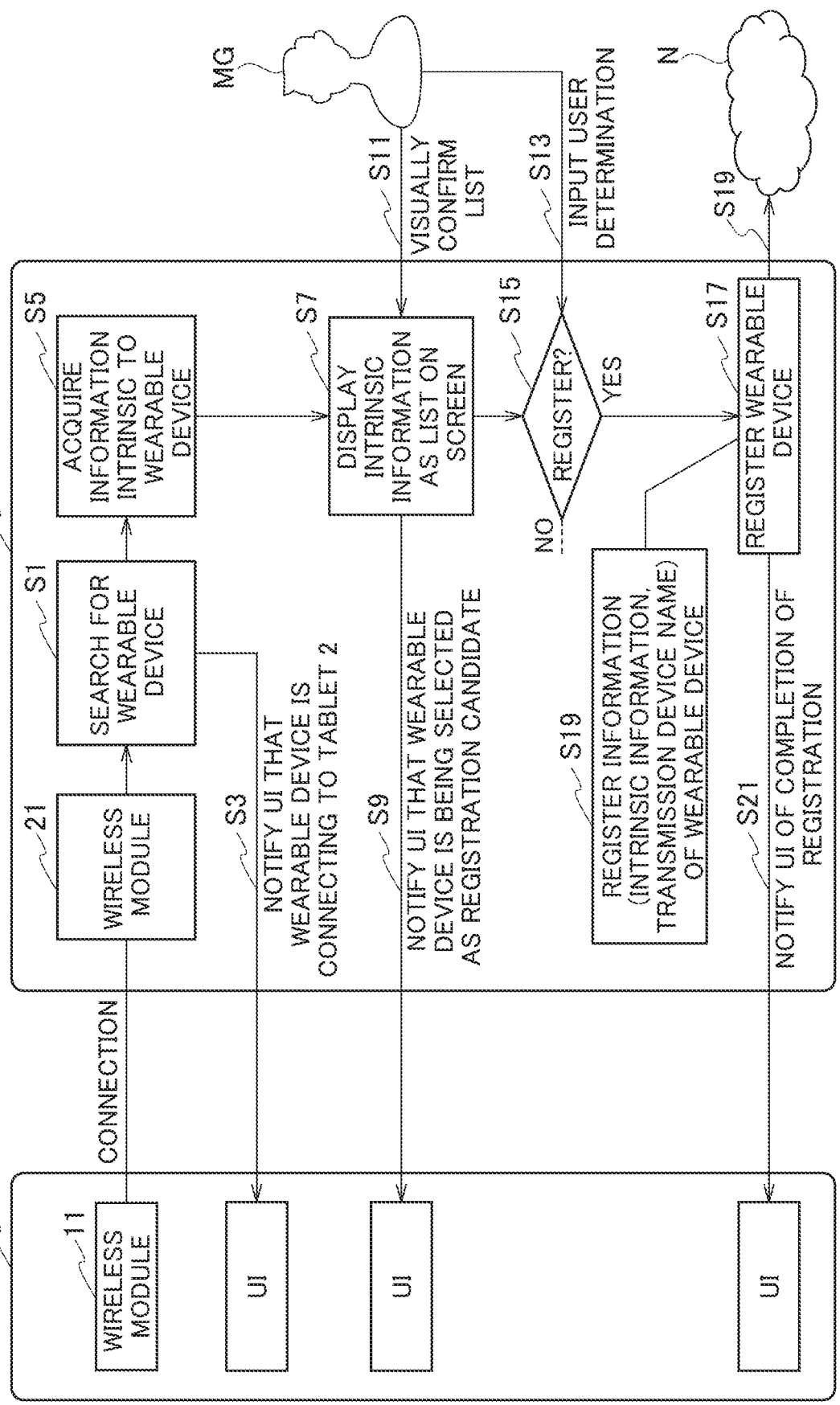
FIG. 3 is an explanatory view of device management in the display device.

FIG. 3 is an explanatory view of device management in the tablet 2.

When the near field wireless communication module 11 of the wearable device 1 and the wireless module 21 of the tablet 2 connect to each other, the tablet 2 detects the wearable device I through the wireless module 21 (Step S1), and notifies a user interface (UI) of the wearable device 1 that the wearable device 1 is connecting to the tablet 2 (Step S3).

Next, the tablet 2 acquires transmission device identification information (a so-called device ID) (Step S4). The device ID is a device address when information added and intrinsic to the wearable device 1 is, for example, information related to Bluetooth (registered trademark), or is a MAC address when the added and intrinsic information is related to Wi-Fi. When there is no information intrinsic to the communication module, the device ID is a profile intrinsic to software of the wearable device 1.

Next, the tablet 2 displays the intrinsic transmission device identification information as a list on a screen (not illustrated) (Step S7), and in addition, notifies the user interface (UI) of the wearable device 1 that the wearable device 1 is being selected as a registration candidate (Step S9).

Next, a user (for example, the manager MG) of the tablet 2 visually confirms the list (Step S11), and inputs a user determination as to whether or not to register the wearable device 1 (Step S13). When the determination to register the wearable device 1 is input (Step S15: YES), the wearable device 1 concerned is registered as the wearable device 1 that connects to the tablet 2 (Step S17). At that time, as the information of the wearable device 1, the intrinsic transmission device identification information and a device name (an arbitrary name) are registered in a cloud (an analysis device 3) and the like through the Internet N (Step S19), and in addition, the user interface (UI) of the wearable device 1 is notified of completion of the registration (Step S21).

(Association between Wearable Device 1 and Tablet 2)

Figure 4:
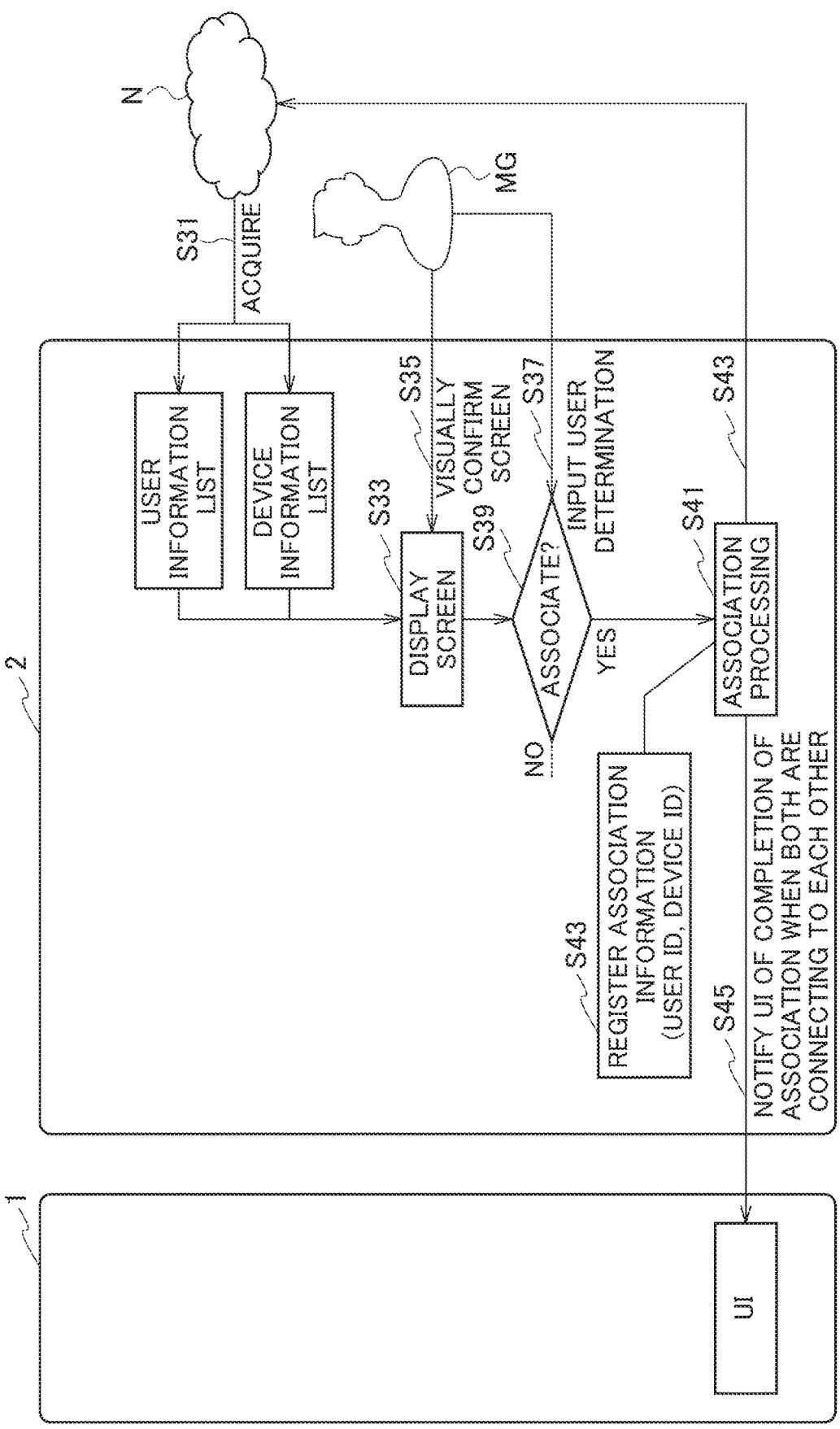
FIG. 4 is an explanatory view of association between the wearable device and the display device.

FIG. 4 is an explanatory view of association between the wearable device 1 and the tablet 2.

First, the tablet 2 acquires a user information list (for example, a name list of such athletes SPi who belong to a team concerned) and a device information list (for example, a list of such device IDs) from the cloud (the analysis device 3) and the like connected to the Internet N (Step S31).

Next, the user information list and the device information list are displayed on the screen (not illustrated (Step S33), and the user (for example, manager MG) of the tablet 2 visually confirms the user information list and the device information list, which are thus displayed (Step S35), and inputs a user determination as to whether or not to perform association between the athlete SPi and the wearable device 1 (Step S37).

When a user determination to perform the association is input (Step S39: YES), the tablet 2 performs association processing for associating the athlete SPi and the wearable device I with each other (Step S41). At that time, in the cloud, the tablet 2 registers, as the association information, the user ID (for example, a registered uniform number) of the athlete SPi, which is registered in the user information list, and the device ID of the wearable device 1, which is registered in the device information list (Step S43), and when the wearable device 1 and the tablet 2 are connecting to each other, the tablet 2 notifies the user interface (UI) of the wearable device 1 of completion of the association (Step S45).

Next, an initial operation and transmission operation of the wearable device 1 will be described.

(Initial Operation of Wearable Device 1)

Figure 5:
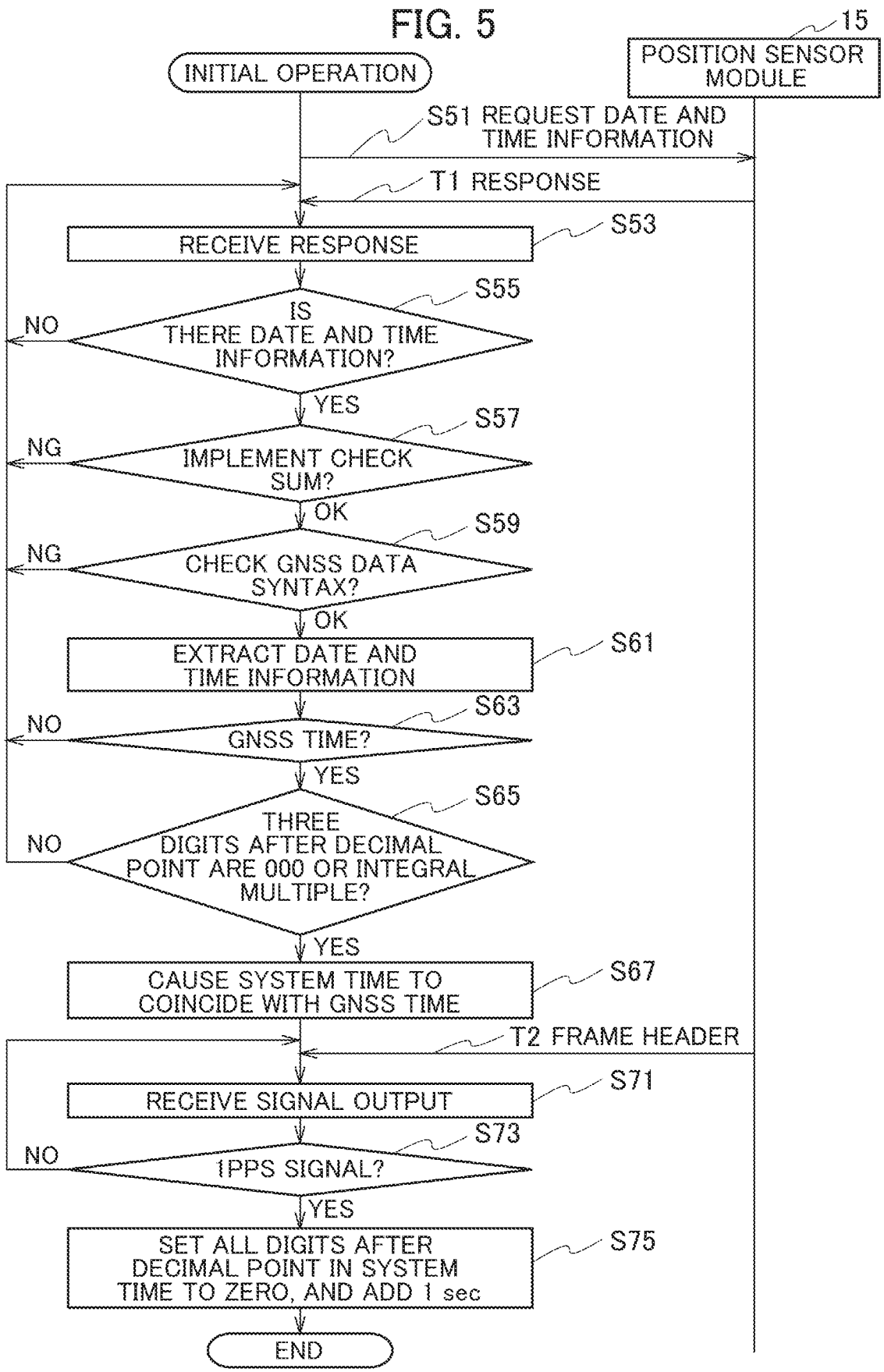
FIG. 5 is a flowchart illustrating an initial operation of the wearable device.

FIG. 5 is a flowchart illustrating the initial operation (time synchronization processing) of the wearable device 1.

The control unit 132 requests date and time information from the position sensor module 15 when the wearable device 1 is started (Step S51). In this way, the position sensor module 15 outputs a response, for example, by Raw data or GNSS data in a format of the National Marine Electronics Association (NMEA) to the control unit 132 (T1).

Upon receiving the response (Step S53), the control unit 132 determines whether the date and time information is present in the response (Step S55), and when the date and time information is not present therein, waits for a response which the position sensor module 15 outputs next, and receives the output response (Step S53).

When the date and time information is present in the response, the control unit 132 implements check sum of a GNSS data format (Step S57), and when the check sum results in no good (NG), waits for and receives a next response (Step S53).

When the check sum results in OK, the control unit 132 checks a syntax of the GNSS data (Step S59), and when the check for the syntax results in NG, waits for and receives a next response (Step S53).

When the check of the syntax results in OK, the control unit 132 extracts the date and time information from the response (Step S61), and determines whether the date and time information is a GNSS time (data and time not in 1980, that is, current data and time) (Step S63). When the date and time information is not the GNSS time, the control unit 132 waits for and receives a next response (Step S53).

When the date and time information is the GNSS time, the control unit 132 performs so-called "0 millisecond confirmation", and determines whether three digits after a decimal point (no more than 1 sec) of the GNSS time is 000 or an integral multiple of 100 (Step S65). When the three digits after the decimal point of the GNSS time is neither 000 nor the integral multiple of 100, the control unit 132 waits for and receives a next response (Step S53).

When the three digits after the decimal point of the GNSS time is either 000 or the integral multiple of 100, the control unit 132 adjusts a time (referred to as a system time) of an internal timer (not illustrated) of its own to the GNSS time (Step S67).

Note that a processing time of Steps S53 to S67 described above is approximately several 10 msec.

Next, the control unit 132 receives a signal output by the position sensor module 15 (T2) (Step S71). For example, the output signal is a frame header including a 1 pulse per second (PPS) signal having one clock waveform per 1 sec. The control unit 132 determines whether the 1PPS signal is present in the output signal (Step S73). When the 1PPS signal is not present, the control unit 132 waits for and receives a next header Step S71).

When the header includes the 1PPS signal, the control unit 132 sets all digits after the decimal point (no more than 1 sec) of the system time to zero, adds 1 sec to the system time (Step S75), and ends the initial operation.

Note that a processing time of Steps S71 to S75 described above is approximately less than 1 msec.

By the initial operation described above, in processes which follow, the GNSS time transmitted together with position data from the position sensor module 15 always coincides with the system time when the GNSS time is received.

Figure 6:
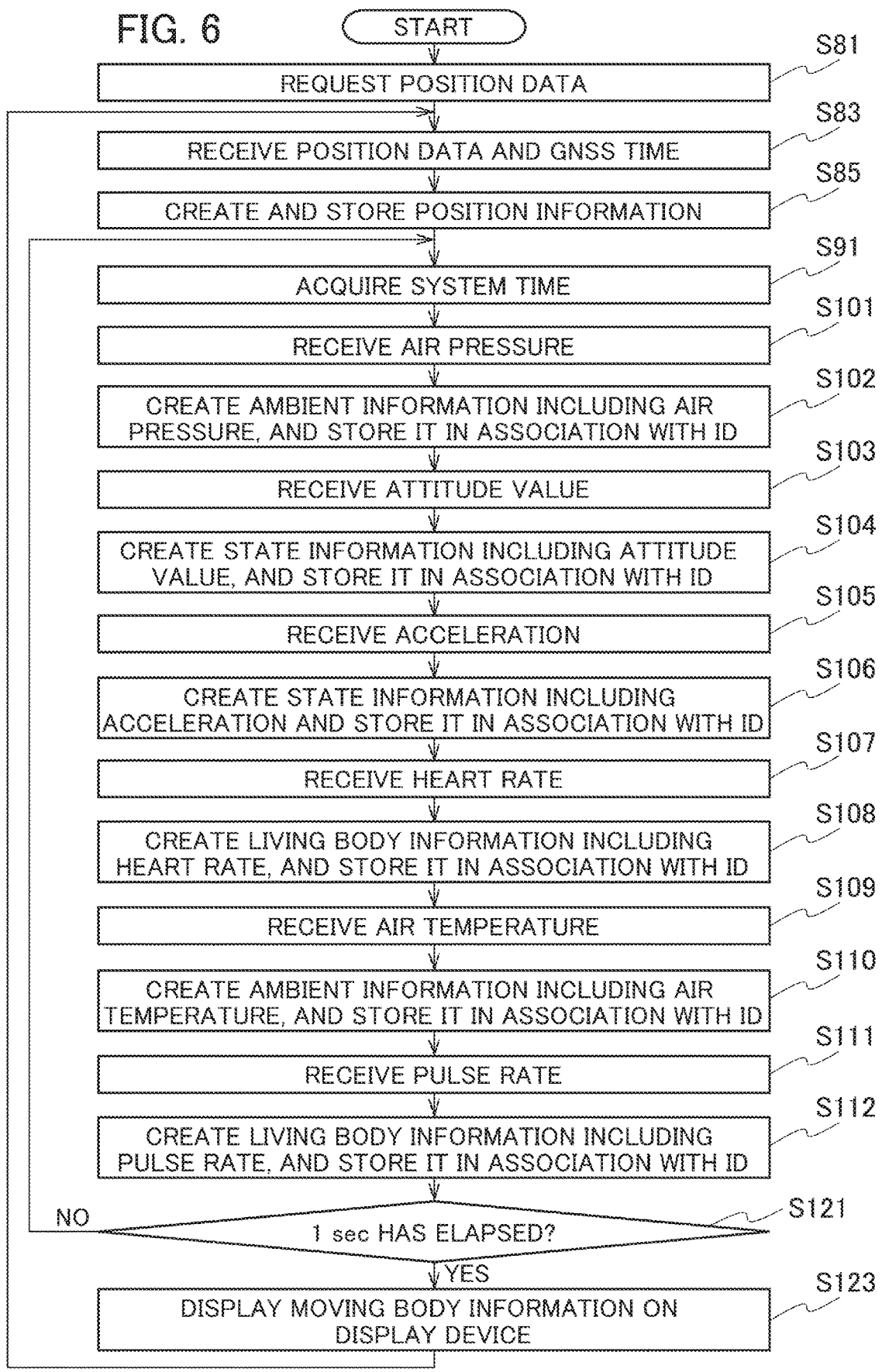
FIG. 6 is a flowchart of processing executed after the initial operation in the wearable device.

FIG. 6 is a flowchart at the when the wearable device 1 transmits moving body information to the tablet 2.

After the initial operation (time synchronization), the control unit 132 of the main control module 13 requests the position data (date and time information) from the position sensor module 15 (Step S81). In this way, the position sensor module 15 transmits the position data and the GNSS time to the control unit 132 periodically (every predetermined time).

Upon receiving the position data and the GNSS time (Step S83), the control unit 132 defines the GNSS time as a position acquisition time, creates position information including the position acquisition time and the position data, and causes the storage unit 131 to store the created position information (Step S85).

Meanwhile, from the living body information detection sensor module 16 other than the position sensor module 15, sensing results (sensor data ESJi) are transmitted to the control unit 132 at pieces of timing intrinsic to the variety of sensors (for the heart rate, the pulse rate . . . ). Likewise, from the ambient information acquisition sensor module 17, sensing results (sensor data TSJi) may be transmitted to the control unit 132 at pieces of timing intrinsic to the variety of sensors (for the air pressure, the air temperature . . . ), and from the state information detection sensor module 18, sensing results (sensor data DSJi) may be transmitted to the control unit 132 at pieces of tinting intrinsic to the variety of sensors (for the gyro force, the acceleration . . . ).

Note that the sensor data ESJi of the living body information detection sensor module 16, the sensor data TSJi of the ambient information acquisition sensor module 17 and the sensor data. DSJi of the state information detection sensor module 18 will be collectively referred to as moving body situation detection data SJi.

If the control unit 132 creates the position information on the basis of the position data and the acquisition time thereof and causes the storage unit 131 to store the created position information, then the control unit 132 acquires the system time in advance (Step S91).

Next, upon receiving, for example, the air pressure from the ambient information acquisition sensor module 17 (Step S101), the control unit 132 creates this air pressure and the system time acquired in Step S91 as the moving body ambient information(STJi), associates, with the moving body ambient information, the position information created in Step S85 immediately therebefore and the ID (the user ID or the device ID) indicating the athlete SPi who wears the wearable device 1, and causes the storage unit 131 to store the moving body ambient information, which is associated with the position information and the ID of the athlete SPi, as moving body information (PJi) (Step S102).

Next, upon receiving, for example, the attitude value from the state information detection sensor module 18 (Step S103), the control unit 132 creates this attitude value and the system time acquired in Step S91 as the moving body state information (SDJi), associates, with the moving body state information, the ID and the position information created in Step S85 immediately therebefore, and causes the storage unit 131 to store the moving body state information, which is associated with the ID and the position information, as the moving body information (PJi) (Step S104).

Next, upon receiving, for example, the acceleration from the state information detection sensor module 18 (Step S105), the control unit 132 creates this acceleration and the system time acquired in Step S91 as the moving body state information (SDJi), associates, with the moving body state information, the ID and the position information created in Step S85 immediately therebefore, and causes the storage unit 131 to store moving body state information, which is associated with the ID and the position information, as the moving body information (PJi) (Step S106).

Next, upon receiving, for example, the heart rate from the living body information detection sensor module 16 (Step S107), the control unit 132 creates this heart rate and the system time acquired in Step S91 as the moving body living body information (SEJi), associates, with the moving body living body information, the ID and the position information created in Step S85 immediately therebefore, and causes the storage unit 131 to store the moving body living body information, which is associated with the ID and the position information, as the moving body information (PJi) (Step S108).

Next, upon receiving, for example, the air temperature from the ambient information acquisition sensor module 17 (Step S109), the control unit 132 creates this air temperature and the system time acquired in Step S91 as the moving body ambient information (STJi), associates, with the moving body ambient information, the ID and the position information created in Step S85 immediately therebefore, and causes the storage unit 131 to store the moving body ambient information, which is associated with the ID and the position information, as the moving body information (PE) (Step S110).

Next, upon receiving, for example, the pulse rate from the living body information detection sensor module 16 (Step S111), the control unit 132 creates this pulse rate and the system e acquired in Step S91 as the moving body living body information (SEJi), associates, with the moving body living body information, the ID and the position information created in Step S85 immediately therebefore, and causes the storage unit 131 to store the moving body living body information, which is associated with the ID and the position information, as the moving body information (PJi) (Step S112).

Next, the control unit 132 determines whether 1 sec has elapsed from the reception of the position data and the GNSS time in Step S83 immediately therebefore (Step S121), and returns to Step S91 when 1 sec has not elapsed. In this way, the moving body living body information SEE such as the heart rate and the pulse rate, the moving body state information such as the attitude value and the acceleration and the moving body ambient information STJi such as the air pressure and the air temperature are created again, and the ID and the position information created in Step S85 immediately therebefore, are associated therewith, and are stored as the moving body information PJi in the storage unit 131.

Meanwhile, when 1 sec has elapsed, the control unit 132 reads out the moving body information PJi, which is not still transmitted to the tablet 2, from the storage unit 131, and transmits the readout moving body information PJi to the tablet 2 (Step S123), and returns to Step S83.

As described above, the control unit 132 sequentially creates the moving body information (the moving body living body information SEJi, the moving body state information SDJi and the moving body ambient information STJi), for example, at a shorter time interval than a time interval (for example, 1 sec) of creating the position information, and associates the moving body information, which is created during a period of creating two pieces of the position information, with either one of the two pieces of position information. In this way, it becomes possible to transmit the moving body living body information SEE, the moving body state information SDJi and the moving body ambient information STJi, which are thus acquired, to the tablet 2 in association with the position information any time.

Figure 7:
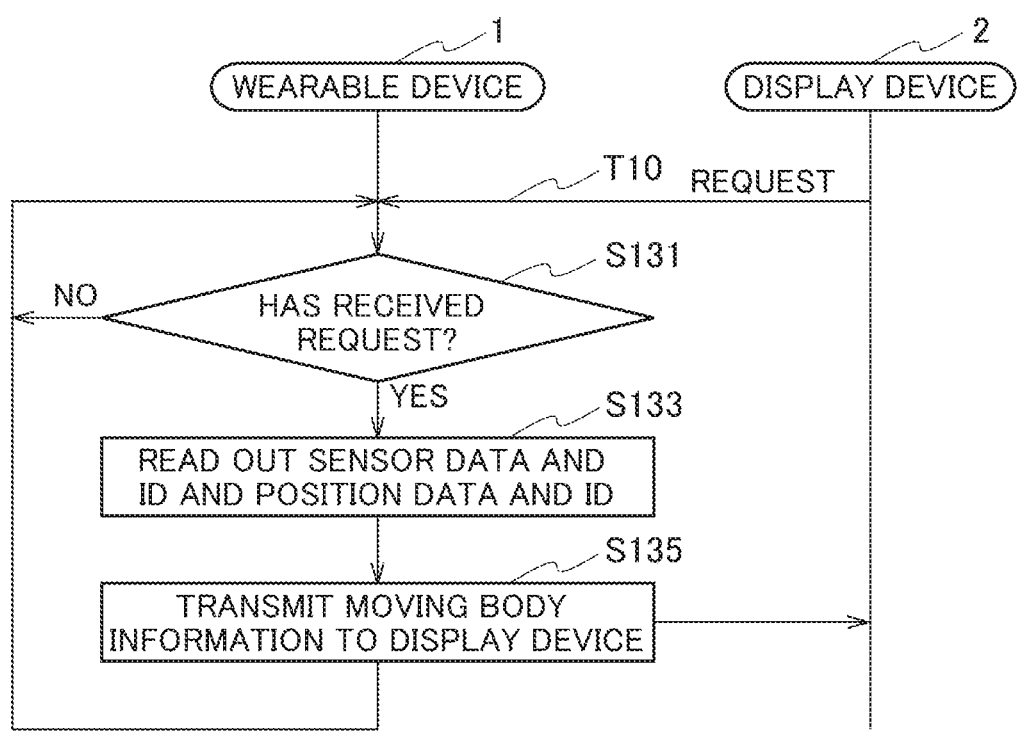
FIG. 7 is a flowchart at the time of causing the wearable device to retransmit moving body information that has been unreceivable by the display device.

FIG. 7 is a flowchart at the time when the wearable device 1 transmits the moving body information, which has not been receivable by the tablet 2, to the tablet 2 again.

The tablet 2 transmits, to the wearable device 1, a request in which there is designated a specific period while the moving body information PJi (the moving body living body information, the moving body state information and the moving body ambient information as well as the position information and the ID) has not been receivable (T10). When a length (for example, 1 sec) of the specific period is predetermined, a start time of the period is designated.

Upon receiving the request from the tablet 2 (Step S31: YES), the control unit 132 of the wearable device 1 reads out the moving body information PJi, which includes the system time included in the period designated in the request, from the storage unit 131 (Step S133), transmits the readout moving body information PJi to the tablet 2 (Step S135), and returns to Step S131.

In this way, the tablet 2 becomes capable of surely receive the moving body information (the moving body living body information SEE, the moving body state information SDJi and the moving body ambient information STJi) in the moving body information PJi unreceivable owing to a communication failure or the like together with the position information and the ID.

Figure 8:
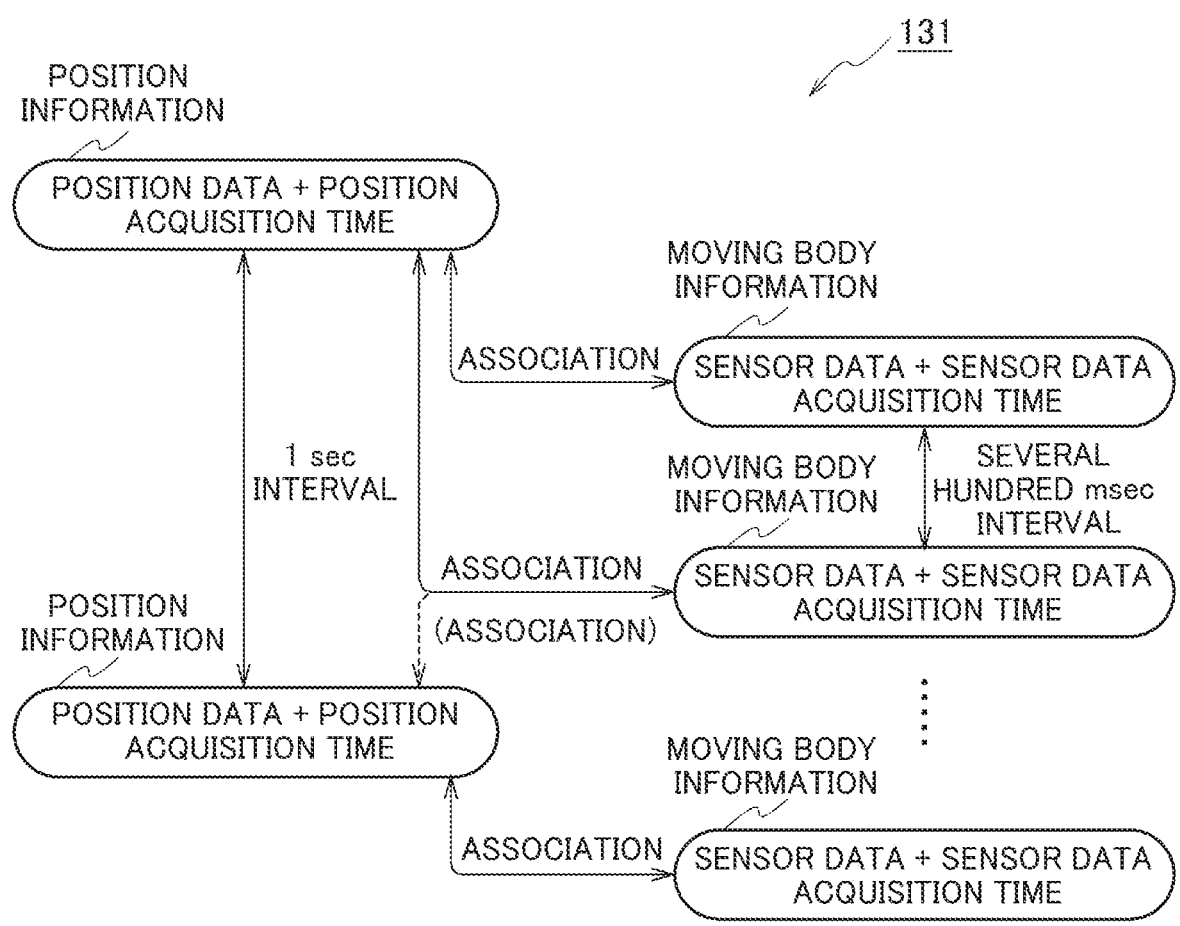
FIG. 8 is a diagram schematically illustrating moving body information managed in a storage unit of the wearable device.

FIG. 8 is a diagram schematically illustrating a state of the storage unit 131.

The position information including such a position acquisition time at an interval of 1 sec is stored in the storage unit 131. Moreover, in the storage unit 131, there is stored moving body information including sensor data at an interval shorter than 1 sec (for example, the interval is an interval of several hundred msec) and including an acquisition time of the sensor data. The position information created immediately therebefore and the ID (not illustrated) are associated with the moving body information.

Note that position information created immediately thereafter and the ID may be associated with the moving body information. In this case, the following procedure just needs to be adopted in which the moving body information is left stored in the storage unit 131 even if the moving body information is created, and when the position information is created next after the laps of 1 sec, this position information and the ID are stored in the storage unit 131 in association with the already acquired moving body information, and are transmitted to the tablet 2. Even in this case, with the moving body information created in such a period of creating two pieces of the position information, associated is either one of the two pieces of position information before and after the moving body information.

In the moving body information thus obtained, the moving body living body information SEJi includes the sensor data ESJi as the moving body situation detection data (the heart rate, the pulse rate . . . ) and the acquisition time of the sensor data, the position information is associated with the moving body living body information SEJi, and the position information includes the position data. The position data is created at substantially the same time as such a sensor data acquisition time, and accordingly, the position data and the sensor data ESJi at substantially the same time are obtained. Likewise, the moving body state information SDJi includes the sensor data DSJi as the moving body situation detection data (the attitude value, the acceleration . . . ) the sensor data acquisition time, the position information is associated with the moving body state information SDJi, and the position information includes the position data. The position data is created at substantially the same time as the sensor data acquisition time, and accordingly, the position data and the sensor data DJi at substantially the same time are obtained. Likewise, the moving body ambient information STJi includes the sensor data TSJi as the moving body situation detection data (the air pressure, the temperature . . . ) and the sensor data acquisition time, the position information is associated with the moving, body ambient information STJi, and the position information includes the position data. The position data is created at substantially the same time as the sensor data acquisition time, and accordingly, the position data and the sensor data TSJi at substantially the same time are obtained.

Then, the collection and analysis application unit 22 of the tablet 2 that has received the moving body information PJi including the moving body information, the position information and the ID, for example, processes received contents appropriately and displays the contents on the screen (not illustrated), and transmits the contents to the analysis device 3. The manager MG who has seen the contents becomes capable of easily grasping the current situation such as the condition of the athlete SPi and the environment of the sports arena.

Meanwhile, the application service unit 31 of the analysis device 3 receives the moving body information Ph (the moving body living body information (the heart rate, the pulse rate . . . ), the moving body state information (the attitude value, the acceleration . . . ), the moving body ambient information (the air pressure, the air temperature . . . ) as well as the position information and the ID), which is sent from the tablet 2, and performs a variety of information analyses.

For example, it is assumed that, when the athlete SPi is a soccer player SPai, position data and an acceleration at the same time are obtained for a certain same ID (the same soccer player). When many relatively high accelerations are associated with specific position data (for example, a position before an opponents goal), that soccer player SPai can be determined to be excellent in instantaneous power at the position before the opponent's goal and suitable for a position of a forward.

Moreover, when many relatively high heart rates and pulse rates are associated with specific position data (for example, a position before a friends' goal) irrespective of such IDs, a team concerned can be determined to be probably more upset than necessary before the friends' goal.

Moreover, when an attitude value associated with specific position data (for example, a position near a side line) changes little with regard to a certain same ID (the same soccer player SPai), that soccer player SPai can be determined to contact little with soccer players of the opponent team near the side line and suitable for a position of a side back.

The application service unit 31 of the analysis device 3 stores such an analysis result, which is thus obtained, in the database 32. Moreover, the analysis device 3 displays the analysis result on the screen (not illustrated), and transmits the analysis result to the tablet 2. For example, the analysis result may be displayed on the screen (not illustrated) of the tablet 2, and may be usable by the manager MG or a staff such as a trainer.

Note that, in the above-described first embodiment, the ID is used to identify the athlete SPi; however, the ID is also unnecessary when it is unnecessary to identify the athlete SPi. For example, the ID is unnecessary in the case of obtaining moving body information of an athlete (living body) as a single home country person who joins a track race.

Moreover, a computer program for causing a computer to function as the wearable device 1 can be recorded in a computer-readable recording medium such as a semiconductor memory, a magnetic disk, an optical disc, a magneto-optical disk and a magnetic tape, and moreover, can be widely distributed by being transferred through a communication network such as the Internet.

Here, a description will be given of another example at the time when the wearable device 1 transmits the moving body information PJi to the tablet 2.

<Modified Example of First Embodiment>

Figure 9A:
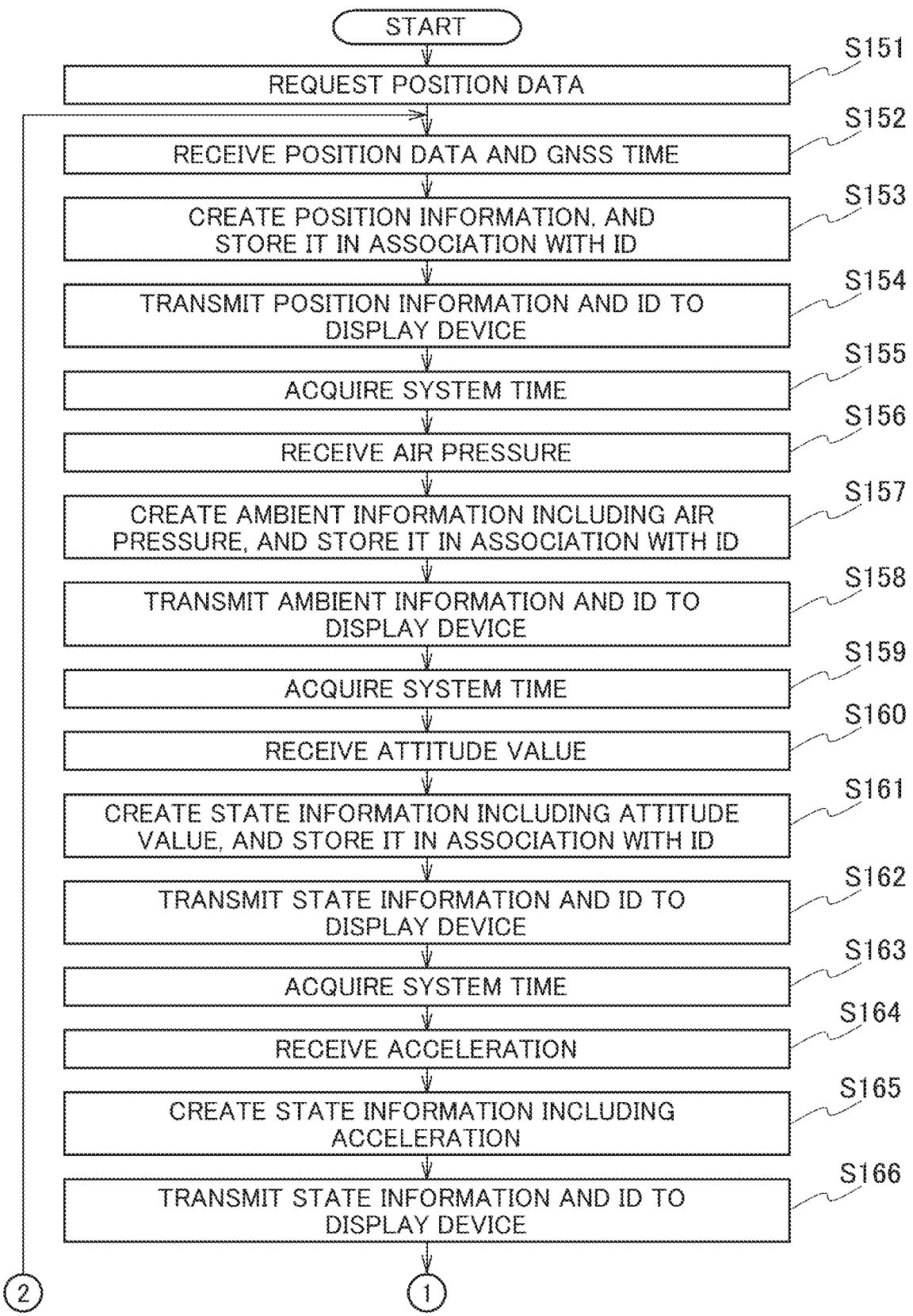

FIGS. 9A and 9B show a flowchart at the time when the wearable device 1 transmits the moving body information PJi to the tablet 2 according to a modified example of the first embodiment.

After the initial operation (time synchronization), the control unit 132 of the main control module 13 requests the position data from the position sensor module 15 (Step S151). In this way, the position sensor module 15 transmits the position data and the GNSS time to the control unit 132 every predetermined time (for example, 1 sec).

Upon receiving the position data and the GNSS time (Step S152), the control unit 132 defines the GNSS time as the position acquisition time, creates the position information including the position acquisition time and the position data, and causes the storage unit 131 to store the created position information in association with the ID (for example, the device ID of the wearable device 1) (Step S153).

Then, the control unit 132 transmits the stored position information and ID as the moving body information to the tablet 2 (Step S154).

Next, after transmitting the position information and the ID to the tablet 2, the control unit 132 acquires the system time (Step S155).

Next, upon receiving, for example, the air pressure from the ambient information acquisition sensor module 17 (Step S156), the control unit 132 creates this air pressure and the system time acquired in Step S155 as the moving body ambient information, associates, with the moving body ambient information, the ID and the position information created in Step S153 immediately therebefore, and causes the storage unit 131 to store the moving body ambient information, which is associated with the ID and the position information (Step S157).

Then, the control unit 132 transmits the stored moving body ambient information, position information and ID as the moving body information to the tablet 2 (Step S158).

Next, after transmitting the moving body ambient information, the position information and the ID to the tablet 2, the control unit 132 acquires the system time (Step S159).

Next, upon receiving, for example, the attitude value of the state information detection sensor module 18 (Step S160), the control unit 132 creates this attitude value and the system time acquired in Step S159 as the moving body state information, associates, with the moving body state information, the ID and the position information created in Step S153 immediately therebefore, and causes the storage unit 131 to store the moving body state information, which is associated with the ID and the position information (Step S161).

Then, the control unit 132 transmits the stored moving body state information, position information and ID as the moving body information to the tablet 2 (Step S162).

Next, after transmitting the moving body state information, the position information and the ID to the tablet 2, the control unit 132 acquires the system time (Step S163).

Next, upon receiving, for example, the acceleration from the state information detection sensor module 18 (Step S164), the control unit 132 creates this acceleration and the system time acquired in Step S163 as the moving body state information, associates, with the moving body state information, the ID and the position information created in Step S153 immediately therebefore, and causes the storage unit 131 to store the moving body state information, which is associated with the ID and the position information (Step S165).

Then, the control unit 132 transmits the stored moving body state information, position information and ID as the moving body information to the tablet 2 (Step S166).

Next, after transmitting the moving body state information, the position information and the ID to the tablet 2, the control unit 132 acquires the system time (Step S167).

Next, upon receiving, for example, the heart rate from the living body information detection sensor module 16 (Step S168), the control unit 132 creates this heart ate and the system time acquired in Step S167 as the moving body state information, associates, with the moving body state information, the ID and the position information created in Step S153 immediately therebefore, and causes the storage unit 131 to store the moving body state information, which is associated with the ID and the position information (Step S169).

Then, the control unit 132 transmits the stored moving body state information, position information and ID as the moving body information to the tablet 2 (Step S170).

Next, after transmitting the moving body state information, the position information and the ID to the tablet 2, the control unit 132 acquires the system time (Step S171).

Next, upon receiving, for example, the air temperature from the ambient information acquisition sensor module 17 (Step S172), the control unit 132 creates this air temperature and the system time acquired in Step S171 as the moving body ambient information, associates, with the moving body ambient information, the ID and the position information created in Step S153 immediately therebefore, and causes the storage unit 131 to store the moving body ambient information, which is associated with the ID and the position information (Step S173).

Then, the control unit 132 transmits the stored moving body ambient information, position information and ID as the moving body information to the tablet 2 (Step S174).

Next, after transmitting the moving body ambient information, the position information and the ID to the tablet 2, the control unit 132 acquires the system time (Step S175).

Next, upon receiving, for example, the pulse rate from living body information detection sensor module 16 (Step S176), the control unit 132 creates this pulse rate and the system time acquired in Step S175 as the moving body living body information, associates, with the moving body living body information, the ID and the position information created in Step S153 immediately therebefore, and causes the storage unit 131 to store the moving body living body information, which is associated with the ID and the position information (Step S177).

Then, after transmitting the stored moving body living body information, position information and ID as the moving body information to the tablet 2 (Step S178), the control unit 132 returns the processing to Step S152.

Note that, for example as illustrated in FIG. 10, the above-mentioned moving body information includes position data (a latitude E1, a longitude N1) and a system time (YYYY/MM/DD:HH:MM:01.100, where "100" is 100 msec). Then, when the sensor data of the moving body living body information is the heart rate, the moving body information becomes information associated with the heart rate.

Figure 11:
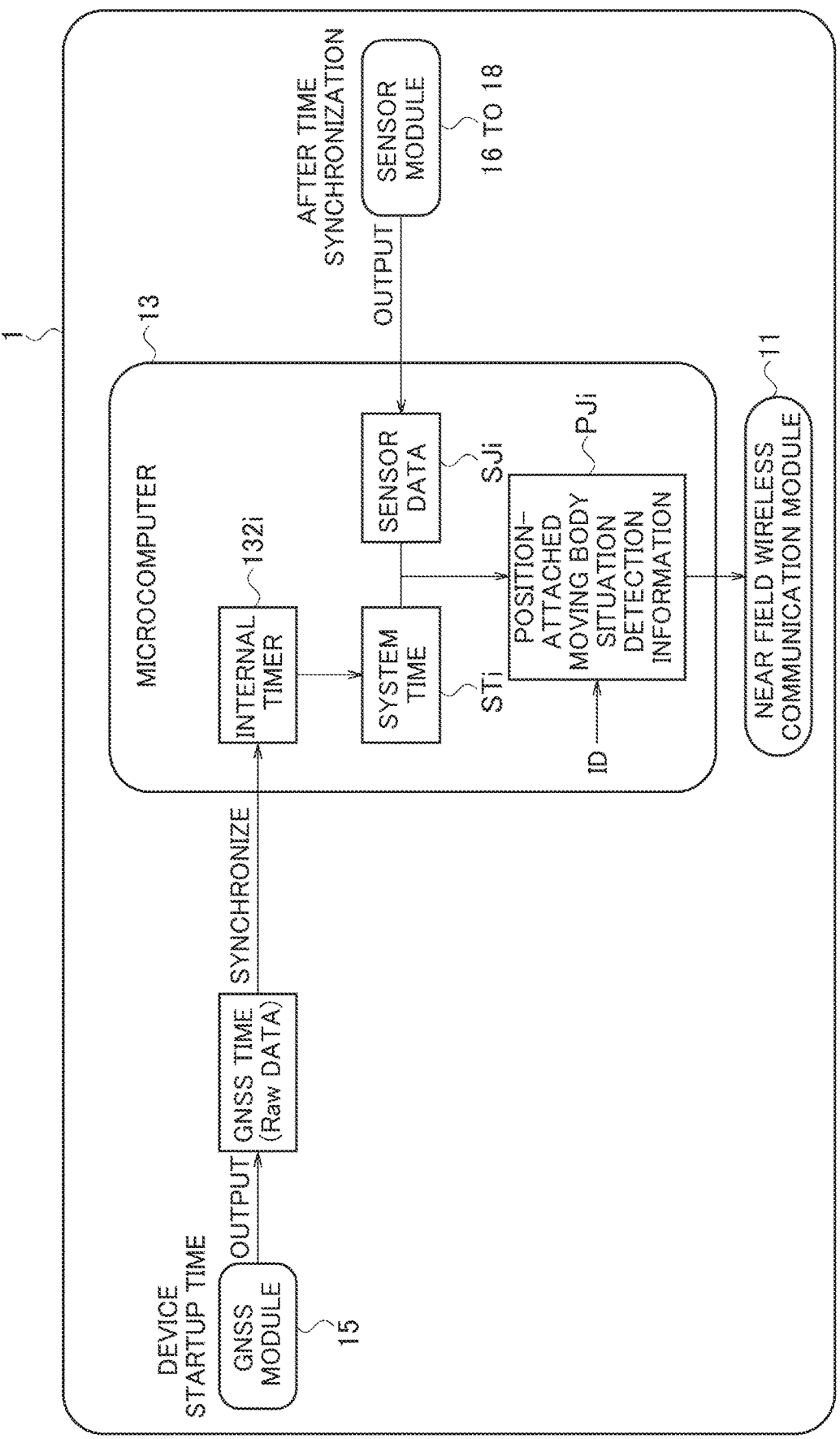
FIG. 11 is a diagram illustrated for explaining an overview of processing (time synchronization) in a main control module of the wearable device.

Herein, a concept of the time synchronization in the above-described wearable device I is illustrated, thr example, as illustrated in FIG. 11.

As illustrated in FIG. 11, the wearable device 1 performs initial synchronization (the time synchronization) between the GNSS time of the position sensor module 15 and the system time of an internal timer 132$i$ of the main control module 13.

Then, after this initial synchronization, the main control module 13 of the wearable device 1 reads the moving body situation detection data SJi that is the sensing results of the sensor modules 16, 17 and 18, At that time, the variety of sensors in the sensor modules 16, 17 and 18 output the moving body situation detection data SJi at pieces of timing, which are intrinsic thereto and different from one another, after the time synchronization.

That is, the main control module 13 reads the sensing results (the moving body situation detection data SJi) of the sensor modules 16, 17 and 18 every time every time when it is the system time STi after the initial synchronization. Then, the main control module 13 defines, as moving body information, a set of the system time STi and the moving body situation detection data SJi at this reading time point, further, associates the moving body information with the position information (that is, creates the moving body information PJi), and thereafter, transmits the moving body information from the near field wireless communication module 11.

Moreover, a concept of the initial operation (the initial synchronization) of the main control module 13 will be described with reference to FIG. 12.

Figure 12:
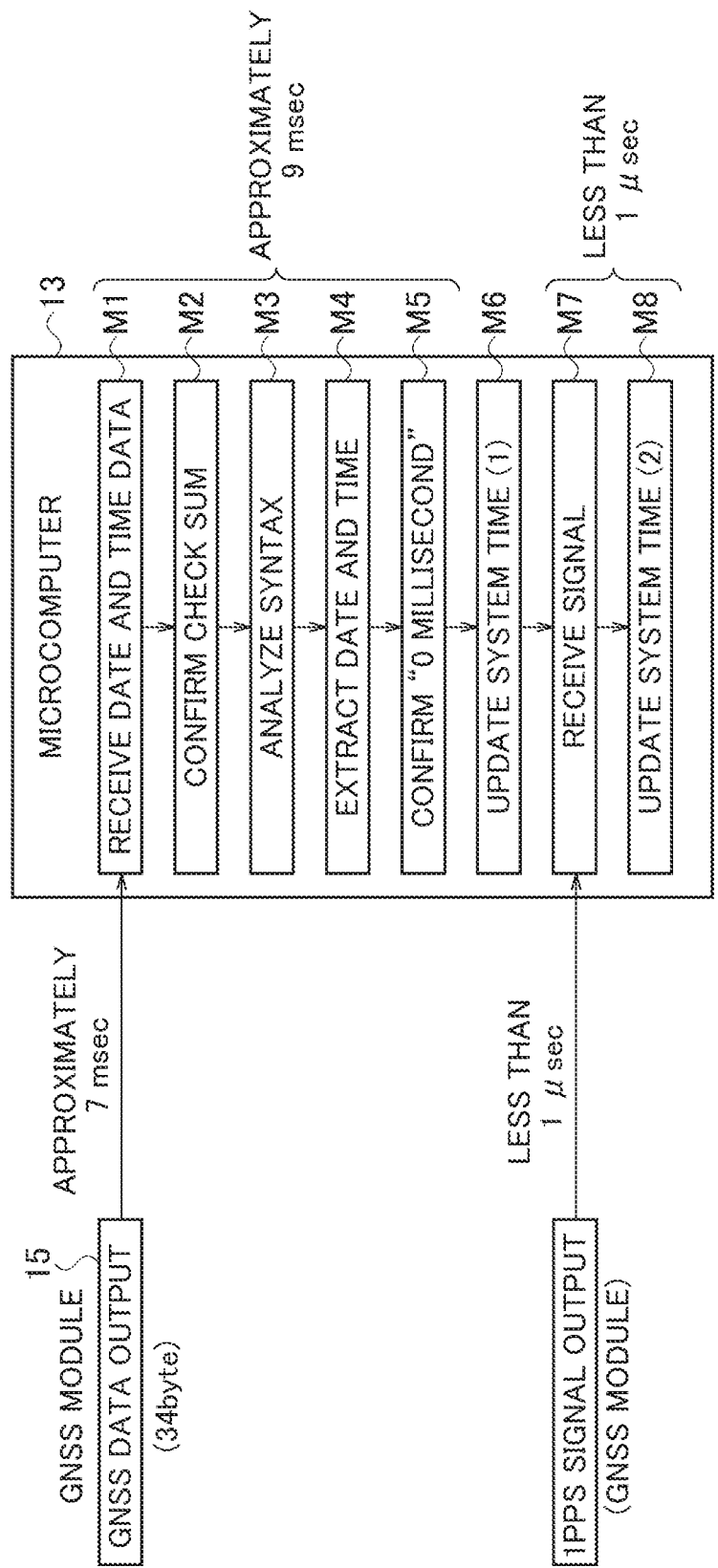
FIG. 12 is a diagram illustrated for explaining a concept of the initial operation in the main control module.

As illustrated in FIG. 12, at the time of the initial synchronization, the main control module 13 first receives date and time data included in the Raw data or the NMEA data (NMEA protocol), which is sent from the position sensor module 15 (M1).

Then, the main control module 13 confirms a check sum of this date and time data (M2), performs syntax analysis (M3), and extracts a date and time (M4).

Thereafter, the main control module 13 performs the "0 millisecond confirmation" (M5), and updates the system time STi (M6).

Then, the main control module 13 receives the 1PPS signal (a reference) sent from the position sensor module 15 (M7), and further updates the system time STi using this 1PPS signal (M8).

Generally, the GNSS time output by the GNSS module is finally settled to the "0 millisecond", and accordingly, the main control module 13 advances the subsequent time update processing (M6) only in the case of having received the GNSS time of the "0 millisecond". That is, the system time is usually delayed from the GNSS time by approximately ten and several milliseconds; however, the delay is at least less than 1 sec. Hence, the system time is updated at the time point of M6, whereby, at the time of having received the 1PPS signal (a time pulse transmitted at an interval of 1 sec and synchronized with the universal time conditioned (UTC)) (M7), a state can be established where the system time is synchronized with the GNSS time at the level of msec by adding 1 sec to the system time (M8).

Second Embodiment

Next, a specific example of the wearable device 1 as the above-described moving body information detection terminal will be described as a second embodiment.

Figure 13:
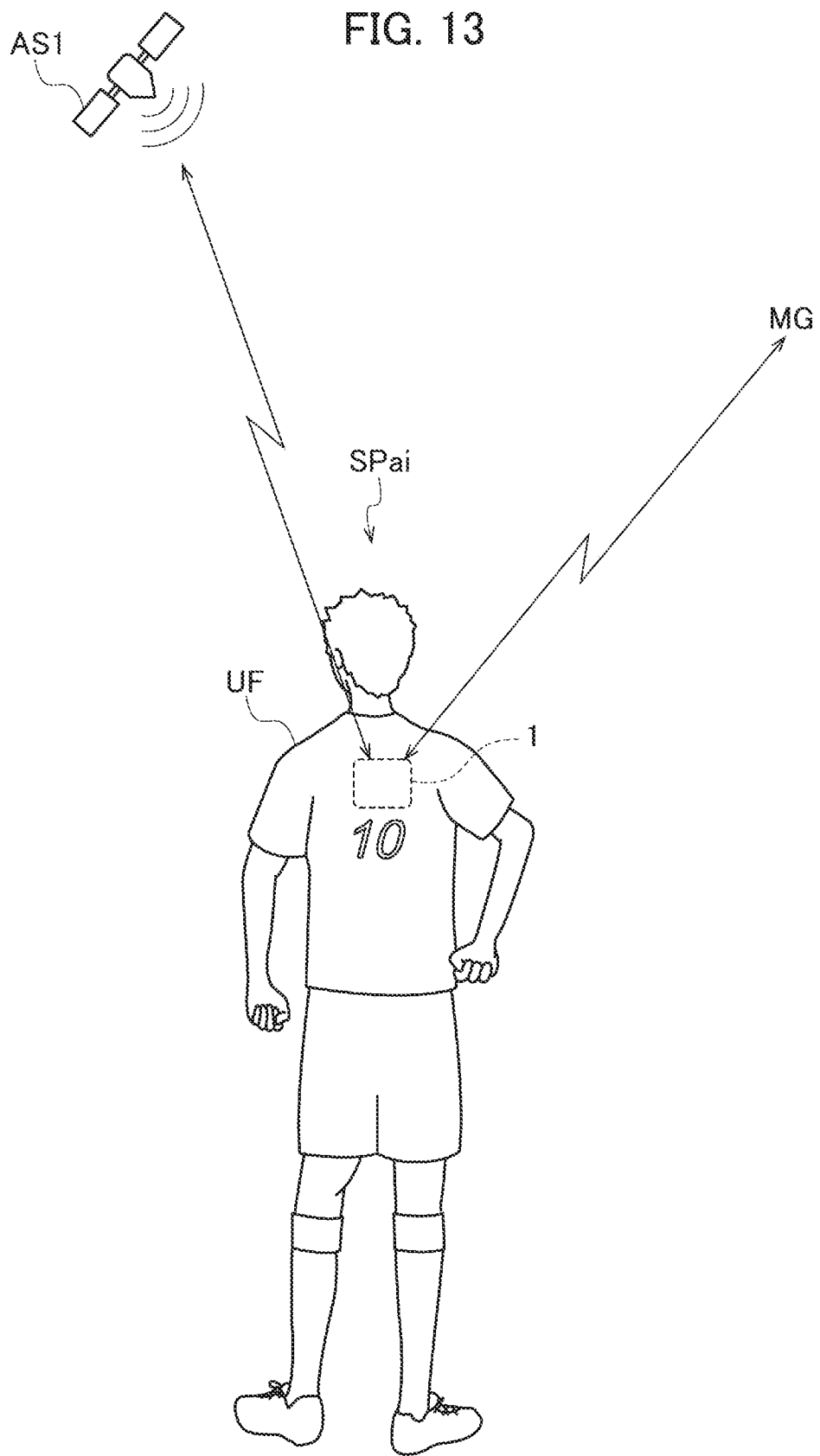
FIG. 13 is a view illustrating a mounting example of a moving body information detection terminal (a wearable device) according to a second embodiment.

In the second embodiment, a description will be given of an example where the wearable device 1 is mounted on a uniform UF of the soccer player SPai as a moving body (living body) as illustrated in FIG. 13. Moreover, the wearable device 1 is mounted on such a standing soccer player SPai so that the position sensor module 15 is located closer to the head thereof.

Figure 14:
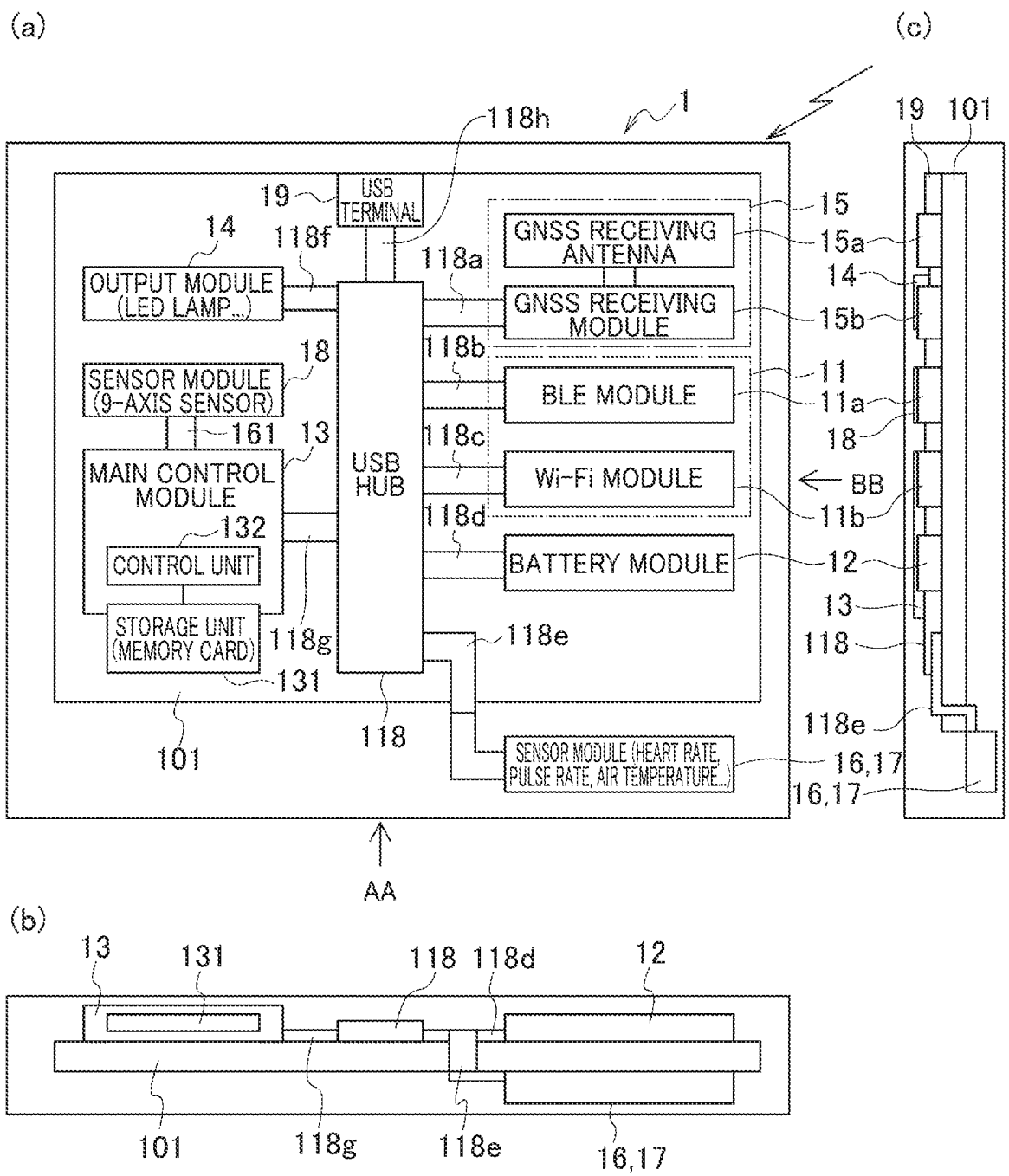
FIG. 14 is diagrams illustrating a schematic configuration of the wearable device.

FIG. 14 is a specific configuration diagram of the wearable device 1. The wearable device 1 is formed into an integrated circuit (IC); however, will be described using a block diagram in order to facilitate the understanding. Note that FIG. 14(a) schematically illustrates a plan configuration of the wearable device 1, FIG. 14(b) schematically illustrates a side surface configuration in an illustrated AA direction of the wearable device and FIG. 14(c) schematically illustrates a side surface configuration in an illustrated BB direction of the wearable device 1.

In FIG. 14(a) FIG. 14(c), a position sensor module 15, a living body information detection sensor module 16, an ambient information acquisition sensor module 17 and a state information detection sensor module 18 will be described as examples of the sensor modules.

FIG. 14(a) to FIG. 14(c), the wearable device 1 includes a near field wireless communication module 11, a battery module 12, a main control module 13, an output module 14, the position sensor module 15, the living body information detection sensor module 16, the ambient information acquisition sensor module 17, the state information detection sensor module 18, a universal serial bus (USB) hub 118, and a charging and externally connecting USB terminal 19 and the like, all of which are mounted on a mounting board (also referred to as a base) 101.

Moreover, for example, the near field wireless communication module 11 includes a Bluetooth (registered trademark) Low Energy (BLE) module 11a and a Wi-Fi module 11b, and at the time of communication with the tablet 2, establishes a connection therewith using initial connection setting information (described later) set by the main control module 13, and continues the communication.

The position sensor module 15 is a high-sensitivity position detection module (GNSS module), and for example, includes a GNSS receiving antenna 15a and a GNSS receiving module 15b. Moreover, the living body information detection sensor module 16 includes sensors acquiring the moving body living body information SEJi of the soccer player SPai, for example, which are a heart rate sensor 16A that acquires the heart rate, a pulse rate sensor 16B that acquires the pulse rate. The living body information detection sensor module 16 outputs sensing results, which are acquired by the respective sensors at pieces of timing, which are intrinsic thereto, as the sensor data ESJi. Moreover, the ambient information acquisition sensor module 17 includes sensors acquiring the moving body ambient information STJi around the soccer player SPai, for example, which are an air pressure sensor 17A and an air temperature sensor 17B which acquire the environment information such as an air pressure and air temperature of soccer field. The ambient information acquisition sensor module 17 outputs sensing results, which are acquired by the respective sensors at pieces of timing, which are intrinsic thereto, as the sensor data TSJi. The respective, sensor modules 15, 16 and 17 are connected to a control unit 132 of the main control module 13 through a USB hub 118.

In contrast, the state information detection sensor module 18 is a 9-axis sensor for acquiring the moving body state information SDJi such as an attitude, speed and the like of the soccer player SPai. For example, in order to detect the sensor data DSJi in units of 100 msec, the state information detection sensor module 18 is directly connected to the main control module 13 through a signal line (an inter-Integrated circuit (I2C)/serial peripheral interface (SPI) or the like) 161. That is, the state information detection sensor module 18 acquires and outputs such sensing results of the attitude value, acceleration, direction (geomagnetism) and the like of the soccer player SPai at pieces of timing, which are intrinsic thereto.

Herein, the control unit 132, the storage unit 131 and the like are provided as the main control module 13 of the wearable device 1.

Although details will be described later, for example, the control unit 132 includes a central processing unit (CPU) with an operation frequency of 1 gigahertz (GHz), a random access memory (RAM) with a capacity of 512 megabytes (MB), and the like. The RAM (hereinafter, referred to as a "memory") functions as a working memory of the CPU, and for example, temporarily stores the created position information, moving body living body information and the like. For example, in this memory, there are previously ensured a memory region for storing the moving body situation detection data SJi from the variety of sensor modules (hereinafter, the memory region will be referred to as a "sensor data storage region 131c").

The storage unit 131 (that may be an SD memory card or the like) is, for example, defined to have a capacity of 16 gigabytes (GB), and is used as a storage for storing a startup program and data. In place of the RAM, this storage unit 131 may be used as a memory.

The USB hub 118 is connected to the main control module 13 through a USB bus (signal cable) 118g.

To respective ports (not illustrated) of the USB hub 118, there are individually connected; the GNSS receiving module 15b of the position sensor module 15 through a USB bus 118a; the BLE module 11a of the near field wireless communication module 11 through a USB bus 118b; the Wi-Fi module 11b of the near field wireless communication module 11 through a USB bus 118c, the battery module 12 through a USB bus 118d; the living body information detection sensor module 16 and the ambient information acquisition sensor module 17 through a USB bus 118e; the output module 14 through a USB bus 118f; and the USB terminal 19 through a USB bus 118h.

The USB hub 118 monitors such input ports (not illustrated) periodically (for example, in units of several msec), and in the case of finding an input port that has received a signal, outputs the signal to the main control module 13. Moreover, for example, the USB hub 118 outputs a signal, which is sent from the main control module 13, to the corresponding BLE module 11a or Wi-Fi module 11b.

The GNSS receiving module 15b is connected to the GNSS receiving antenna 15a, and every 1 sec, generates the 1PPS signal included in the frame header, and outputs the Raw data of the GNSS data, which is sent from the GNSS satellite AS1 and received through the GNSS receiving antenna 15a, to the main control module 13 through the USB hub 118. Moreover, the GNSS receiving module 15b uses a global positioning system (GPS), a satellite-based augmentation system (SBAS) and a quasi-zenith satellite system (GNSS). In the GNSS receiving module 15b, an update rate is set to 1 to 20 Hz, position accuracy is set to 2.5mCEP, a velocity accuracy is set to 0.1 m/sec, a warm start time to first fix (TTFF) is set to 29 sec in average, and a cold start TTFF is set to 30 sec in average. Moreover, in the GNSS receiving module 15b, cold start sensitivity is set to −148 dBm, tracking sensitivity is set to −165 dbm, and at accuracy of 10 nsec (+/−), a GNSS clock (an internal timer, not illustrated) is synchronized with the 1PPS signal (a time reference P1PPs).

The BLE module 11a is a near field wireless communication module that transmits and receives data according to the Bluetooth (registered trademark) protocol.

The Wi-Fi module 11b is a near field wireless communication module for a wireless local area network (LAN), which is authenticated by the Wi-Fi Alliance.

The battery module 12 is, for example, a lithium polymer battery pack, a lithium ion polymer battery or the like, in which a charged amount is set to approximately 2500 mAh. The battery module 12 is set usable for five to six hours.

The output module 14 may include, for example, an LED lamp, a vibrator, a buzzer and the like for reporting that the battery is now being charged, reporting a residual amount, and so on (not illustrated).

The USB terminal 19 is used for charging the battery module 12, and for a connection to an external instrument (for example, a personal computer; not illustrated).

The living body information detection sensor module 16 is the heart rate sensor 16A and the pulse rate sensor 16B. For example, the heart rate sensor 16A acquires heat rate data in a fixed sensing cycle as the sensor data ESJi (SJi), and outputs the heart rate data at this time point of the acquisition to the USB hub 118 through the USB bus 118e.

Figure 15:
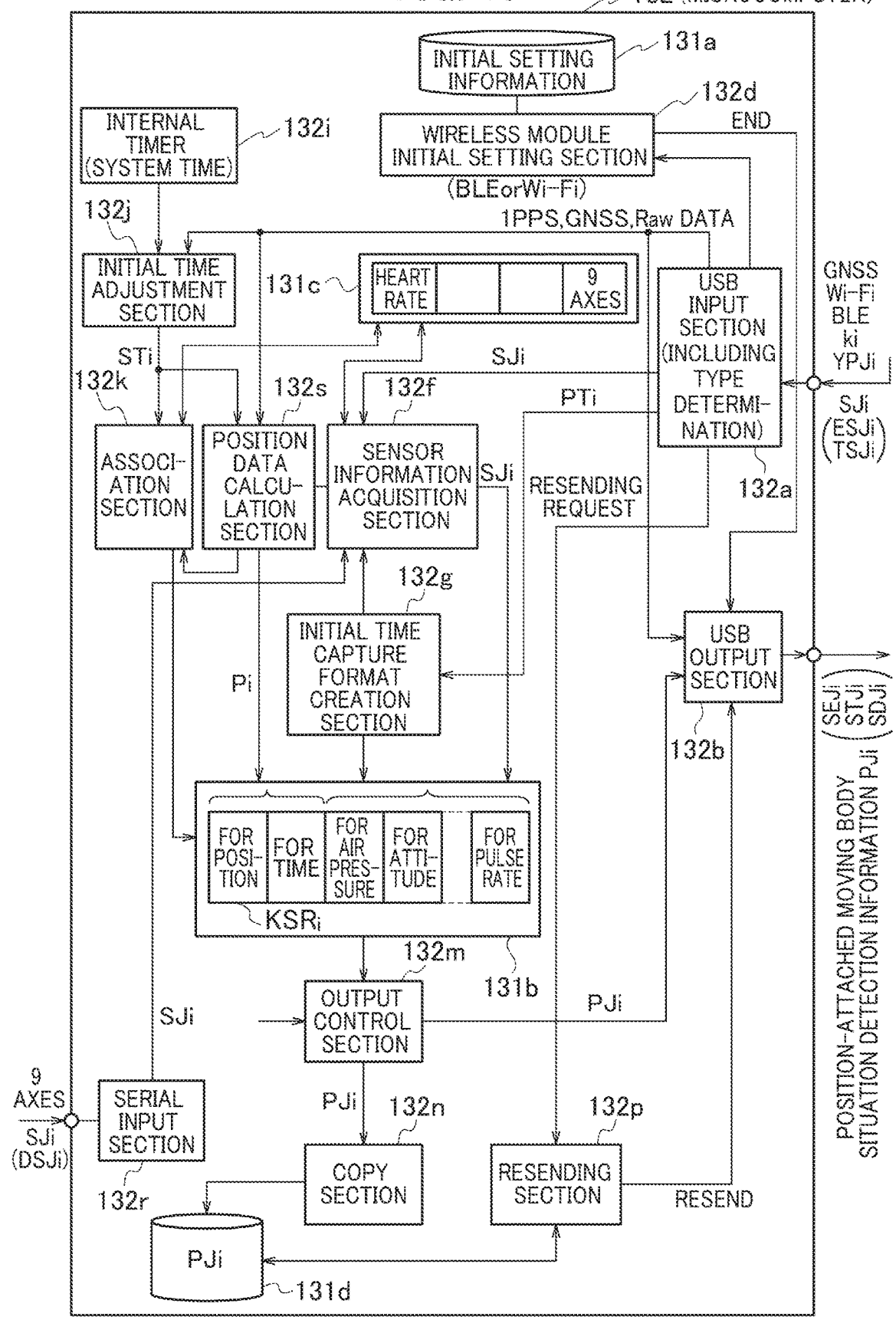
FIG. 15 is a functional block diagram of a control unit that constitutes a main control module of the wearable device.

FIG. 15 illustrates a schematic program configuration (functional blocks) of the control unit 132 in the main control module 13 of the wearable device 1.

The control unit 132 (initially) synchronizes the system time STi of the internal timer 132i with the GNSS time and the Raw data as original data of the position in addition, the control unit 132 creates the moving body information PJi in which the position information of the position sensor module 15 is associated with the moving body living body information SEJi of the heart rate and pulse rate of the soccer player SPai on the soccer field, with the moving body state information SDJi such as the attitude and speed of the soccer player SPai, and with the moving body ambient information STJi around the soccer player SPai. Then, the control unit 132 transmits the created moving body information PJi to the tablet 2.

This system time STi is arbitrary; however, preferably, is caused to coincide with output timing of such a sensor of which detection timing is earliest, for example, at the GNSS time or less. As this system time STi, it is preferable to set an initial time of each of the near field wireless communication module 11 and the tablet 2 when a communication connection o the tablet 2 by the near field wireless communication module 11 is started.

For example, the control unit 132 includes a USB input section 132a, a USB output section 132b, a wireless module initial setting section 132d, a sensor information capture section 132f, an initial time capture format creation section 132g, the internal timer 132i, an initial time adjustment section 132j, an association section 132k, an output control section 132m, a copy section 132n, a resending section 132p, a serial input section 132r, a position data calculation section 132s, and the like.

The internal timer 132i is enabled to output the system time STi no more than the output timing of the position data (Pi).

Through the USB hub 118, the USB input section 132a captures the output from the near field wireless communication module 11, the Raw data of the GNSS receiving module 15b of the position sensor module 15, the sensor data ESJi (SJi) that is the sensing results (the heart rate . . . ) of the living body information detection sensor module 16, and the like. For example, the USB input section 132a is provided with a function that makes it possible to determine types of such inputs thereto. That is, the USB input section 132a receives signals (information) input thereto, determines contents of the signals, and passes the signals (information) to the respective sections in response to results of the determination.

For example, when the input is a transmission format pattern PTi sent from the tablet 2, the USB input section 132a provides this input to the initial time capture format creation section 132g (details will be described later). Moreover, for example, when the input is an instruction command sent from the tablet 2 and regarding initial setting of the near field wireless communication module 11 (at the time of the initial operation), the USB input section 132a provides the input to the wireless module initial setting section 132d.

Moreover, for example, when the input is an input relating to the 1PPS signal or the GNSS time, which is sent from the GNSS receiving module 15b (at the time of the initial operation), the USB input section 132a provides the input to the initial time adjustment section 132j.

Moreover, for example, when the input is the Raw data sent from the GNSS receiving module 15b, or when the input is the sensor data ESJi (SJi) such as the heart rate sent from the living body information detection sensor module 16, the USB input section 132*a* provides the input to the sensor information capture section 132*f*.

Moreover, for example, when the input is a resending request sent from the tablet 2, the USB input section 132*a* provides the input to the resending section 132*p*.

Furthermore, though details will be described later, the USB input section 132*a* is notified of sensor acquisition kinds ki capturable from the tablet 2.

In contrast, the serial input section 132*r* is a sensor that captures the sensor data DSJi (SJi) such as the attitude value and the acceleration from the state information detection sensor module 18, and outputs this sensor data DSJi (SJi) to the sensor information capture section 132*f*.

When a power supply is turned on, the wireless module initial setting section 132*d* starts up the near field wireless communication module 11. Then, every time when the wireless module initial setting section 132*d* receives, through the USB hub 118, a connection request including the device ID of the tablet 2 and sent from the near field wireless communication module 11, the wireless module initial setting section 132*d* transmits, for example, information, which is registered in advance in the storage unit 131 and includes the device ID of the wearable device 1, from the near field wireless communication module 11, and establishes a line connection state.

Initial setting information at this time point of the line connection state is stored in an initial setting information storage memory region 131*a* preset in the memory. Moreover, this initial setting information is stored in the initial setting information. storage memory region 131*a* until the connection is shut down.

Every time when the initial time capture format creation section 132*g* receives, from the USB input section 132*a*, the transmission format pattern PTi sent from the tablet 2, the initial time capture format creation section 132*g* creates a transmission format KSRi (a transmission form), which is based on this transmission format pattern PTi, in a transmission format pattern memory region 131*b* preset in the memory.

For example, as illustrated in FIG. 16(*a*), the initial time capture format creation section 132*g* creates the transmission format KSRi in which a head portion is used for a position and a system time and a subsequent portion is used for sensor data. Then, the initial time capture format creation section 132*g* enters a standby state for the sensor acquisition kinds ki sent from the tablet 2.

In the case of having received the sensor acquisition kinds ki, as illustrated in FIG. 16(*b*), the initial time capture format creation section 132*g* creates sensor data transmitting regions (also referred to as format regions) equivalent to the number, which corresponds to the sensor acquisition kinds ki, in the subsequent portion of the transmission format KSRi in accordance with the sensor acquisition kinds ki, for example, the air pressure, the 9 axes (the attitude value), the 9 axes (the acceleration), the heart rate, the temperature, the pulse rate or a combination of any thereof. That is, a total length of the transmission format KSRi changes in response to the sensor acquisition kinds ki sent from the tablet 2. Hence, the data to be transmitted lightens as the number of sensor acquisition kinds ki sent from the tablet 2 is smaller.

The initial time adjustment section 132*j* receives the 1PPS signal sent from the position sensor module 15 through the USB input section 132*a*, the Raw data serving as a source of the GNSS time and the position data, and the system time STi, and synchronizes the system time STi with the Raw data.

The sensor information capture section 132*f* determines whether the sensor data ESJi (SJi) of the living body information detection sensor module 16 is output from the USB input section 132*a*. When the sensor data is output, the sensor information capture section 132*f* determines the sensor acquisition kinds ki thereof. That is, the sensor information capture section 132*f* determines that the sensor that outputs the sensor data ESJi (SJi) is present.

When the above-described sensor is present, the sensor information capture section 132*f* overwrites and stores the sensor data ESJi (SJi) in the corresponding sensor data storage region 131*c* of the memory. That is, every time when the sensor information capture section 132*f* receives the moving body living body information SEJi such as the heart rate and the pulse rate (which is output at different pieces of timing every fixed time), the sensor information capture section 132*f* captures the moving body living body information SEJi and overwrites and stores the moving body living body information SEJi in the corresponding sensor data storage region 131*c* of the memory.

Moreover, the sensor information capture section 132*f* sequentially overwrites and stores the sensor data DSJi (SJi) of the 9-axis sensor, which is sent through the serial input section 132*r*, in the corresponding sensor data storage region 131*c*.

That is, even if the variety of sensors of the plurality of moving body situation detection sensor modules output the moving body situation detection data, the stored moving body situation detection data SJi is held until the next moving body situation detection data SJi is output. That is, as described in the first embodiment, the position data and the moving body situation detection data at substantially the same time are associated with each other.

Every time when the position data calculation section 132*s* receives the Raw data, the 1PPS signal and the system time STi sent from the initial time adjustment section 132*j*, then on the basis of differences between these and preset reference data, the position data calculation section 132*s* obtains a detection position Pi (a latitude Ei, a longitude Ni) as the position data of the wearable device 1.

Upon receiving a moving body information request signal YPJi, which requests the moving body information PJi sent from the tablet 2, through the near field wireless communication module 11 and the USB input section 132*a*, the association section 132*k* performs association processing for writing the detection position Pi and the system time STi input during the 1PPS signal as header information to the head portion of the transmission format KSRi of the transmission format pattern memory region 131*b*, and writing, to predetermined regions (format regions) of the subsequent portion, the present moving body situation detection data SJi (mutually different in timing) in the sensor data storage region 131*e* at a time point when this system time STi is input (refer to FIG. 16(*b*)). At this time, the association section 132*k* expresses all of the respective data such as the system time STi and the detection position Pi by digit strings in the transmission format KSRi. That is, the respective format regions of the transmission format KSRi are defined by the sensor acquisition kinds ki in advance, and accordingly, even if the respective data are transmitted by this transmission format KSRi, the tablet 2 or the analysis device 3 can decipher the respective data.

All of the respective data in the transmission format KSRi are expressed by digit strings, whereby an amount of data transmittable by the transmission format KSRi can be increased.

Moreover, the digit strings are sorted, or an order of the format regions of the transmission format KSRi, which are defined by the sensor acquisition kinds ki, is changed, whereby it can be made difficult for devices other than the tablet 2 or the analysis device 3 to decipher the respective data.

Every time when the association processing ends, the output control section 132*m* puts the respective sensor data SJi (the sensor data transmitting regions) of the transmission format KSRi of the transmission format pattern memory region 131*b* to one side, defines the put sensor data SJi as the moving body information PJi, and transmits the moving body information PJi through the USB output section 132*b* from the near field wireless communication module 11 to the tablet 2.

That is, the output control section 13 discards (deletes) the sensor data transmitting regions in which the moving body situation detection data SJi is not formatted in the transmission format KSRi, and forms the moving body information PJi only of the sensor data transmitting regions in which the moving body situation detection data SJi is formatted.

The copy section 132*n* copies the moving body information PJi, and stores the moving body information PJi in a predetermined moving body information storing copy region 131*d* defined in the memory in advance.

When a resending request is included in the moving body information request signal YPJi sent from the tablet 2, the resending section 132*p* reads out the moving body information PJi corresponding to this moving body information request signal YPJi from the moving body information storing copy region 131*d*, and resends the moving body information PJi through the USB output section 132*b* to the tablet 2.

Figure 17:
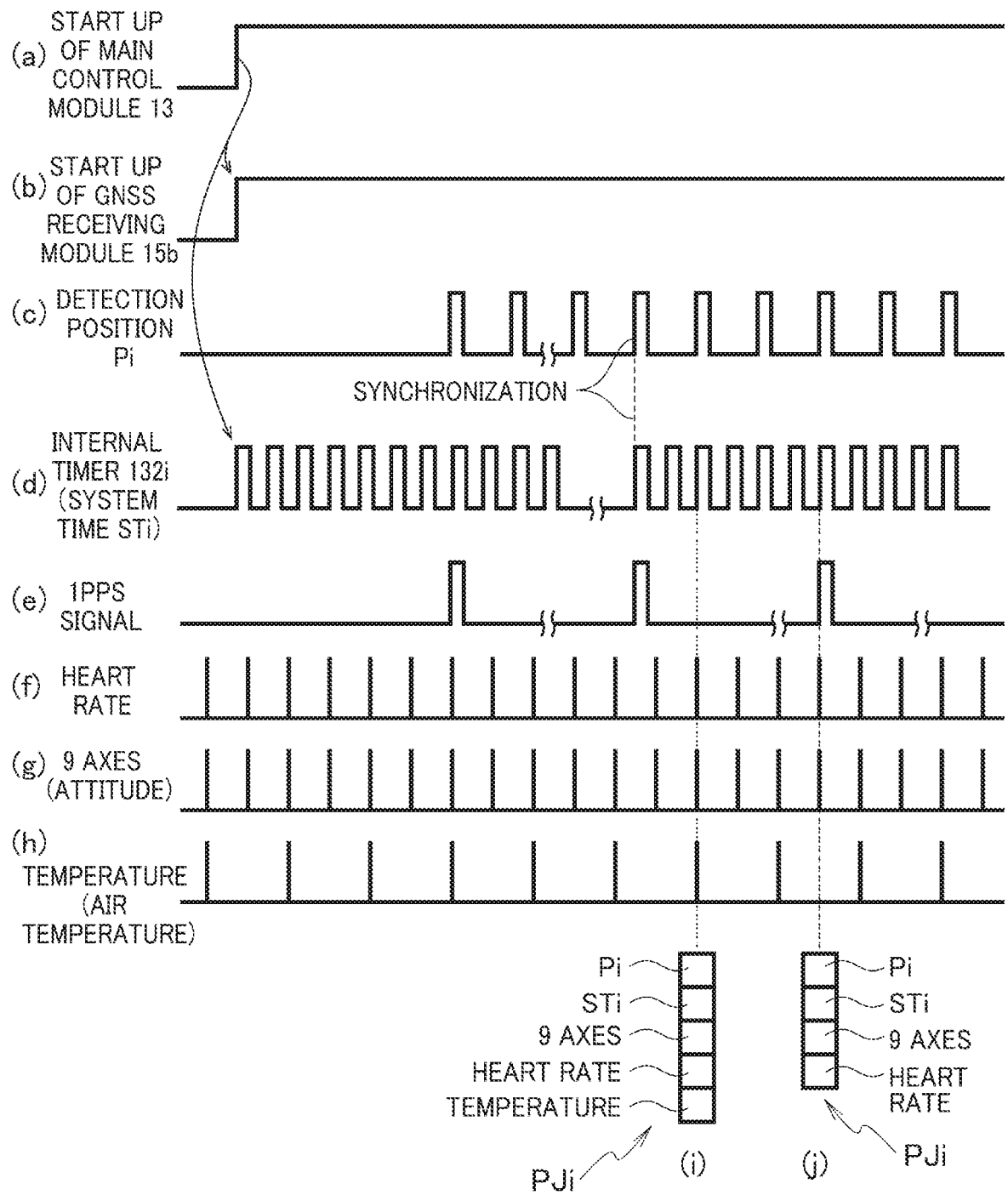
FIG. 17 is a timing chart illustrated for explaining a process up to obtaining the moving body information in the wearable device.

Next, the explanation of the process up to where the wearable device 1 obtains the moving body information PJi will be supplemented using a timing chart of FIG. 17.

FIG. 17(*a*) illustrates startup of the main control module 13, FIG. 17(*b*) illustrates startup of the position sensor module 15, and FIG. 17(C) illustrates output timing of the detection position Pi (including the GNSS time). Moreover, FIG. 17(*d*) illustrates output timing of the system time STi of the internal timer 132*i*, and FIG. 17(*e*) illustrates output timing of the 1PPS signal of the position sensor module 15. Furthermore, FIG. 17(*f*) illustrates output timing of the sensor data ESJi (Sji) of the heart rate, FIG. 17(*g*) illustrates output timing of the sensor data DSJi (SJi) of the 9-axis sensor (for example, the attitude), and FIG. 17(*h*) illustrates output timing of the sensor data (TSJi (SJi) of the temperature.

As illustrated in FIG. 17, following the startup of the main control module 13, the position sensor module 15, the internal timer 132*i* and the variety of sensors start up.

That is, after the Raw data serving as a reference of the detection position Pi and the system time STi are synchronized with each other, the association section 132*k* reads out, from the sensor data storage region 131*c*, the moving body situation detection data SJi at the time point when the system time Sti is output, and writes (overwrites) the moving body situation detection data SJi to a predetermined region of the transmission format KSRi of the transmission format pattern memory region 131*b*.

FIG. 17(*i*) illustrates an example where, as the moving body information PJi, the sensor data ESJi (SJi) of the heart rate, the sensor data DSJi (SJi) of the 9-axis sensor and the sensor data TSJi (SJi) of the temperature coincide with one another in terms of timing at a time point when the detection position Pi is output, and these are therefore taken out and formatted into the transmission format KSRi. Moreover, FIG. 17(*j*) illustrates an example where the sensor data ESJi (SJi) of the heart rate and the sensor data DSJi (SJi) of the 9-axis sensor coincide with each other in terms of timing at a time point when the detection position Pi is output, and these are therefore taken out and formatted into the transmission format KSRi.

That is, even if the variety of sensors of the moving body situation detection sensor module output the moving body situation detection data SJi at different pieces of timing, all types of the moving body situation detection data SJi held at the present time point can be formatted onto the transmission format KSRi at a time closest to the system time STi (or at the same time) (association processing).

Then, following the end of this association processing, the output control section 132*m* puts the respective data of the transmission format KSRi to one side to form the moving body information PJi, and thereafter, transmits the moving body information Ph through the USB output section 132*b* from the near field wireless communication module 11 to the tablet 2.

Figure 18:
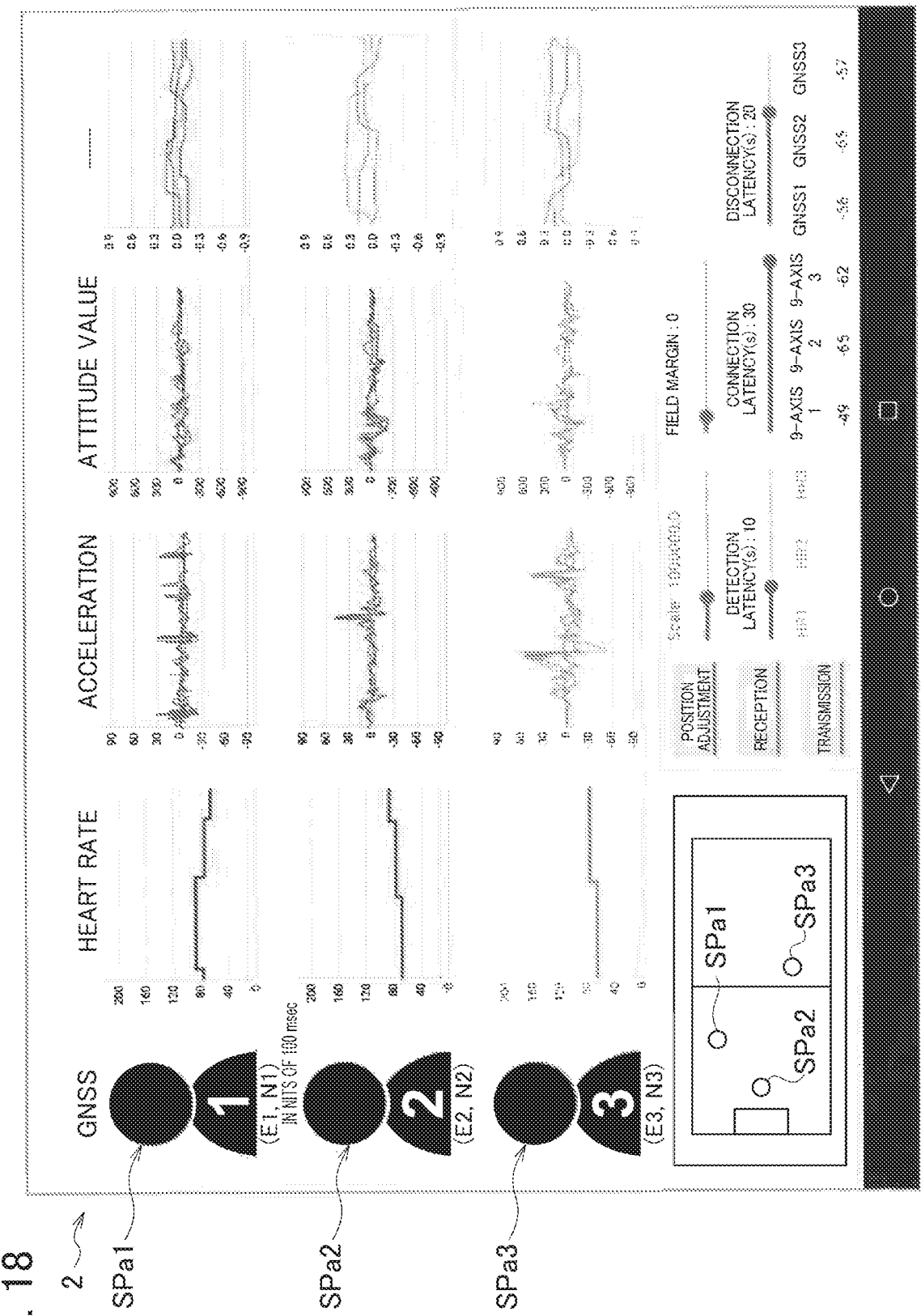
FIG. 18 is a view illustrating an example of displaying, on the display device, the moving body information coming from the wearable device.

Hence, as illustrated in FIG. 18, it is made possible for the tablet 2 to display the moving body information PJi in which the heart rates, the accelerations, the attitude values and the like are associated with the detection positions N of the soccer players SPai. Therefore, in units of the detection position Pi in real time, there can be grasped where and how which of soccer players SPa1, SPa2, SPa3 . . . has moved, how the moving body living body information SEJi at that time has been, and so on.

Moreover, use of the analysis result of the analysis device 3 also makes it possible to display a comparison between the present moving body information and the past moving body information with regard to the same soccer player SPai on the screen of the tablet 2.

Third Embodiment

Figure 19:
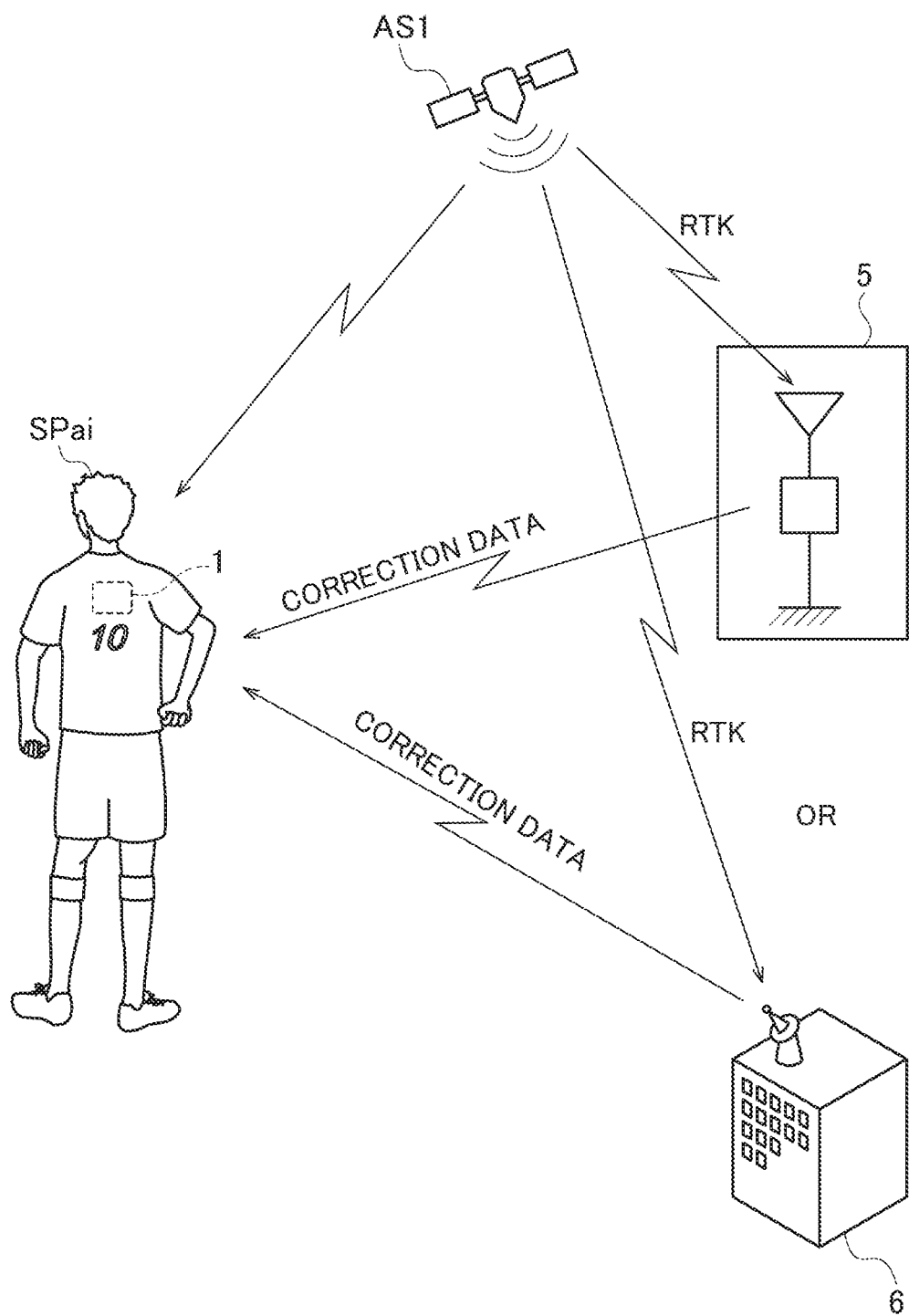
FIG. 19 is a view illustrating an RTK correction technology in a moving body information detection terminal (a wearable device) according to a third embodiment.

FIG. 19 illustrates a concept of a third embodiment

This third embodiment is an example of the case where positioning accuracy of the detection position Pi by the wearable device 1 is always maintained to be high by adopting the realtime kinematic (RTK) positioning technology.

As illustrated in FIG. 19, every time when the wearable device 1 obtains the detection position Pi, the wearable device 1 is caused to transmit correction data of this detection position Pi to a reference position providing station by wireless communication. The reference position providing station is composed, for example, of a reference station 5 or a reference position service center 6.

That is, the reference station 5 or the reference position service center 6 obtains correction data, for example, that is a difference between a positioning result based on GNSS data sent from a GNSS satellite AS1 and an actual reference position, and transmits the obtained correction data to the wearable device 1. Then, on the basis of the received correction data, the wearable device 1 that has received this correction data corrects the detection position Pi of the soccer player SPai concerned, and in addition, executes the above-mentioned association processing in response to the corrected detection position Pi. In this way, the detection position Pi with high accuracy is always maintained.

Figure 20:
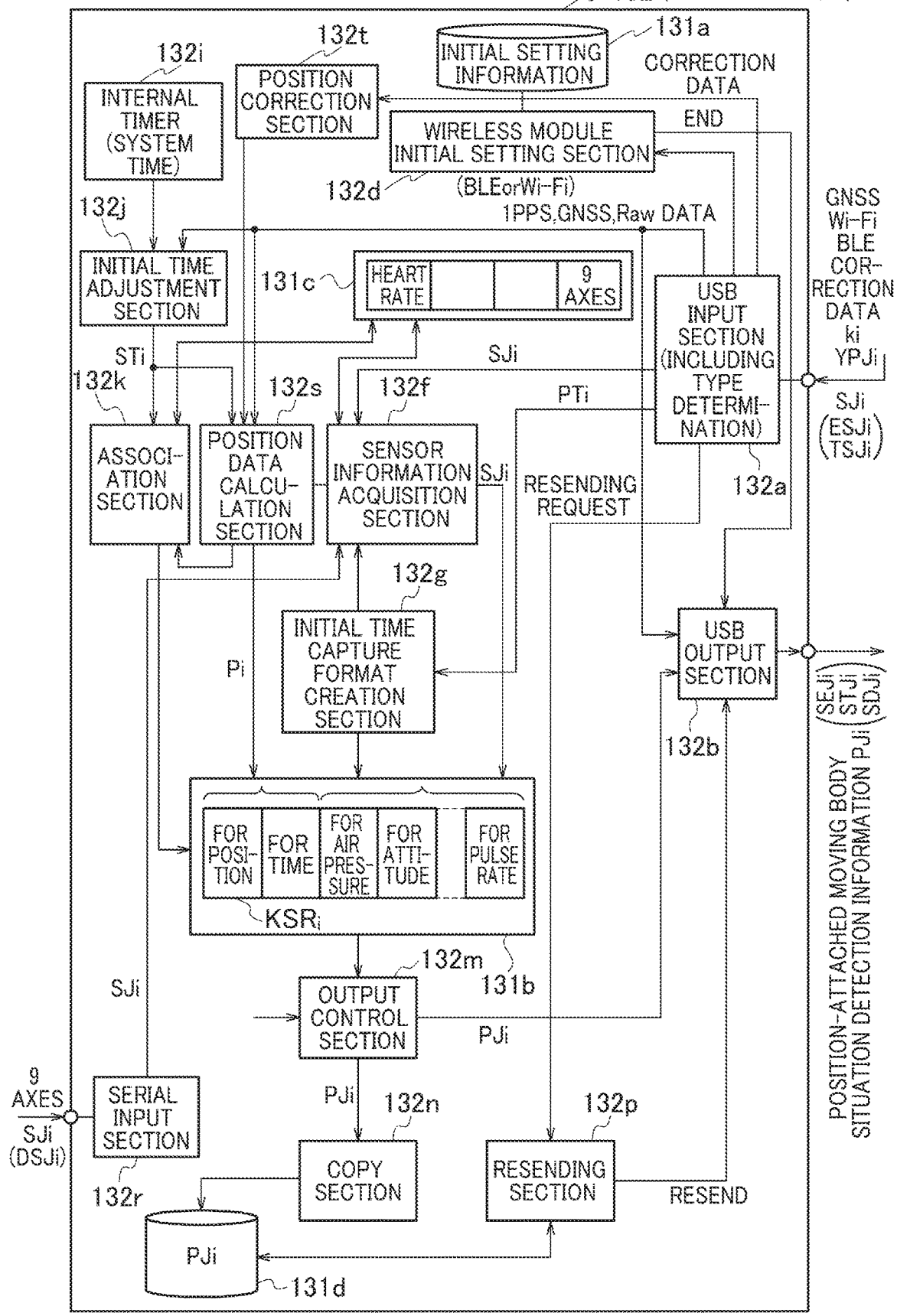
FIG. 20 is a functional block diagram of a control unit that constitutes a main control module of the wearable device, the functional block diagram being illustrated for explaining the RTK correction processing in the wearable device.

FIG. 20 is a specific configuration diagram of a main control module 13 of a wearable device 1 according to a third embodiment. In FIG. 20, the same or similar reference numerals are assigned to the same portions as in the second embodiment, and a detailed description thereof will be omitted.

In the third embodiment, the control unit 132 in the main control module 13 further includes a position correction section 132t. For example, every time when the Wi-Fi module 11b of the near field wireless communication module 11 receives the correction data sent from the reference position providing station, this position correction section 132t captures the correction data through the USB input section 132a. Then, the detection position Pi of the wearable device 1, which is calculated in the position data calculation section 132s, is corrected by the correction data received by the position correction section 132t.

Subsequently, as described in the second embodiment, the corrected detection position Pi is used in the creation of the transmission format KSRi, whereby the positioning accuracy of the detection position Pi can always be maintained to be high.

Fourth Embodiment

Figure 21:
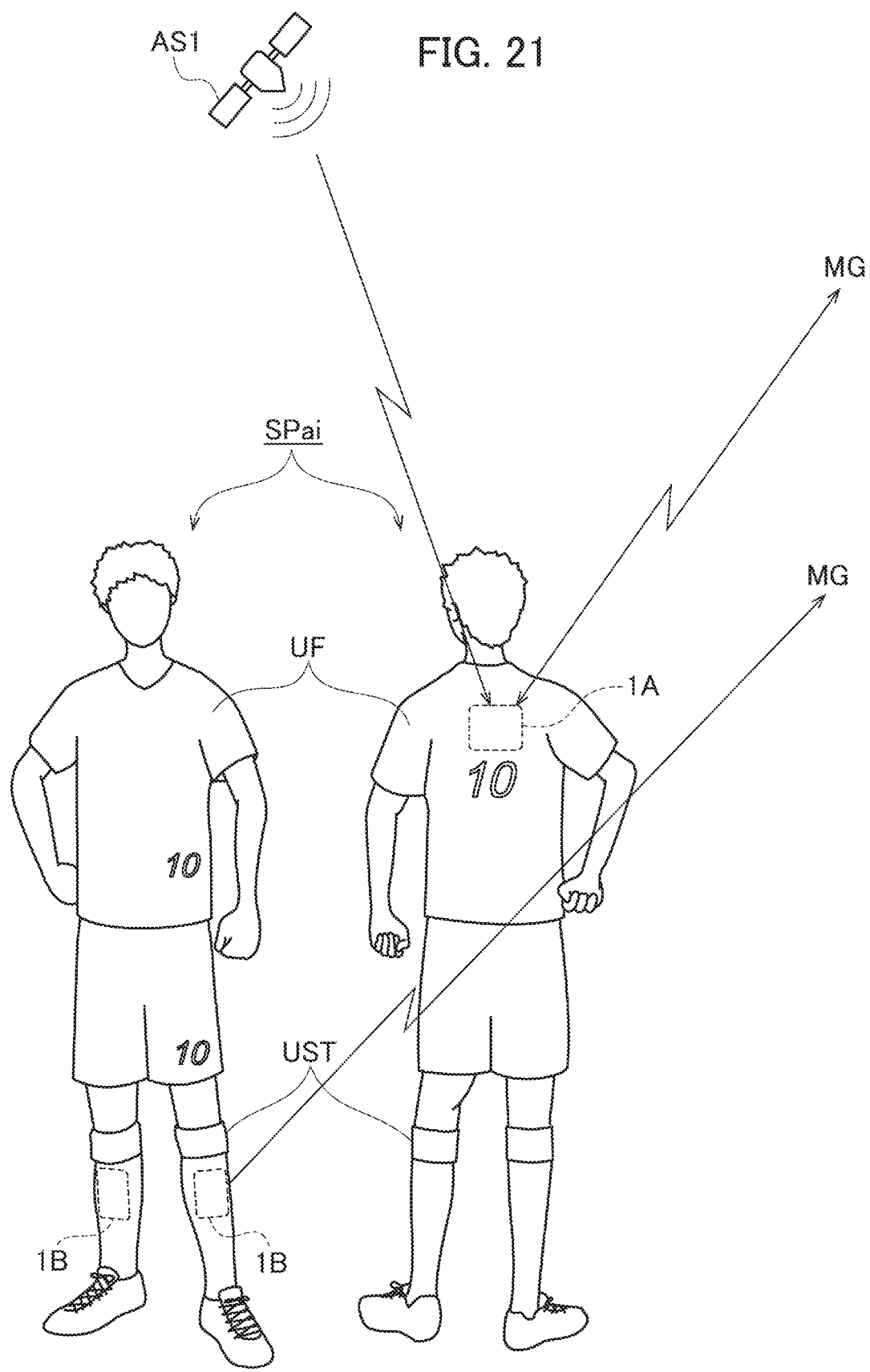
FIG. 21 is a schematic diagram illustrating a configuration example of a moving body information detection terminal (a wearable device) according to a fourth embodiment.

As a fourth embodiment, for example, as illustrated in FIG. 21, a back wearable device 1A (moving body information detection terminal) may be mounted in an inside of a back portion of a uniform UF of the soccer player SPai, and leg wearable devices 1B (moving body information detection terminals) may be mounted on insides (in shin guards) of stockings UST of the uniform UF.

The back wearable device 1A and the leg wearable devices 1B according to this fourth embodiment may each have a similar configuration to that of the above-mentioned wearable device 1, and for example, the position data, the heart rate and the like may be sensed by the back wearable device 1A, and the acceleration and the like may be sensed by the leg wearable devices 1B. That is, such a configuration can also be adopted, in which the hack wearable device 1A includes the position sensor module 15 and the living body information detection sensor module 16 that senses the heart rate and the like of the soccer player SPai, the leg wearable devices 1B include the state information detection sensor modules 18 which acquire the moving body state information such as the attitude value, acceleration and the like of the soccer player SPai, and the leg wearable devices 1B communicate with the tablet 2 through the wearable device 1A.

<Supplementary Explanation of Transmission Format KSRi>

During a play and exercise of soccer, in sonic eases, an external person (for example, a supporter or the like) attempts to acquire information on an athlete.

Preferably, the above-mentioned transmission format KSRi is ciphered by the following method so that a safe communication can be made even in such a case.

Generally, the ciphering increases an amount of data, and sometimes brings about a decrease of a communication speed. Therefore, for example as illustrated in FIG. 16(a), the initial time capture format creation section 132g creates the transmission format KSRi in which a head portion is used for a position and a system time and a subsequent portion is used for sensor data. Then, the initial time capture format creation section 132g enters a standby state for the sensor acquisition kinds ki sent from the tablet 2.

In the case of having received the sensor acquisition kinds ki, as illustrated in FIG. 16(b), the initial time capture format creation section 132g creates sensor data transmitting regions equivalent to the number, which corresponds to the sensor acquisition kinds ki, in the subsequent portion (a region for the sensor data) of the transmission format KSRi in accordance with the sensor acquisition kinds ki, for example, the air pressure, the 9 axes (the attitude value), the 9 axes (the acceleration), the heart rate, the temperature, the pulse rate or a combination of any thereof. That is, the total length of the transmission format KSRi changes in response to the sensor acquisition kinds ki sent from the tablet 2. Hence, the data to be transmitted lightens as the number of sensor acquisition kinds ki sent from the tablet 2 is smaller.

Moreover, when an amount of data transmittable at a time is assumed to be 32 bytes, data to be transmitted is limited to numbers as much as possible, and the number of bits for use per letter (per number) is set to 4 bits for example, whereby it becomes possible to virtually transmit data with up to 64 bytes. In addition, the data to be transmitted is limited to numbers as much as possible, whereby it can be made difficult to estimate contents thereof.

Moreover, regularity may be imparted to an arrangement pattern of the data to be transmitted (for example, a digit string of 64 bytes), that is, the data to be transmitted. may be ciphered by sorting the numbers every time when the data is transmitted.

Furthermore, not only an actual time is transmitted as the system time, but also a time difference between the wearable device 1 and the tablet 2 or the like may be transmitted for example.

Note that the variety of sensors of the moving body situation detection sensor module are not limited to the heart rate sensor, the 9-axis sensor and the like, and for example, may be sensors for living body information such as a body temperature and a sweat rate and environment information such as an illumination intensity, a luminous intensity, a humidity, an air speed, an air direction and a rainfall. Alternatively, when the moving body is a non-living body such as a drone, a sensor that senses vibrations and the like can also be applied. The variety of sensors are made composable by directly using commercially available sensors, whereby cost of the wearable device can be reduced.

Moreover, the moving body (living body) is not limited to an athlete, and may be a child, an elderly person or the like, and for example, the wearable device can also be applied to watching of a child in geo-fence such as a recreational area including an amusement park and a park, or care for a care user in a nursing facility or a hospital.

Moreover, the wearable device is also suitable for use in monitoring a vibration, sound, altitude, air pressure, depth and weight of a heavy machine such as an agricultural machine and a construction machine or of a drone or robot introduced into a disaster site or in sensing water quality and a gas concentration at a site which a person cannot enter as well as in such a living body as an athlete and an animal.

Each of the described functions and processes can be implemented by one or more processing circuits. The processing circuits include a programmed processor, electric circuit and the like, and further, can include a device such as an application specific integrated circuit (ASIC) and circuit constituents disposed to execute the described function.

As above, the present invention has been described by the embodiments; however, it should not be understood that the description and the drawings, which form a part of this disclosure, limits the present invention. For those skilled in the art, varieties of alternative embodiments, examples and application technologies will be obvious from this disclosure.

It is natural that the present invention incorporates a variety of embodiments which are not described herein. Hence, the technical scope of the present invention is defined only by items specifying the invention, which are according to the scope of claims reasonable based on the above description.

The present disclosure claims priority based on Japanese Patent Application No. 2016-193860 filed on Nov. 30, 2016, and priority based on Japanese Patent Application No. 2017-154125 filed on Aug. 9, 2017, and the entire contents of these two applications are incorporated herein by reference.

INDUSTRIAL APPLICABILITY

In accordance with the present invention, the moving body situation detection information detected by the variety of sensors is sampled at the system time no more than the output interval of the Raw data that is original data of the GLASS position information. Accordingly, it is possible to incorporate the plurality of sensors different in acquisition timing, and the moving body situation detection information that is outputs of the variety of sensors can be acquired as much as possible at the same time as the system time. Moreover, the acquired moving body situation detection information is transmitted to the external device in association with the system time and with the position information. Accordingly, even if the moving body moves fast, the external. device can calculate an accurate position thereof, and this accurate position can be displayed in association with each piece of the moving body situation detection information. Therefore, the external device can finely grasp where and how the moving body stands at the present time point. For example, when the moving body is a soccer player, a user (a manager or a coach) of the external device can grasp under which situation and how the player moves at a certain spot in units of the detection position.

DESCRIPTION OF REFERENCE NUMERALS 1 wearable device
1A back wearable device
1B leg wearable device
2 tablet
3 analysis device
5 reference station
6 reference position service center
11 near field wireless communication module
11a BLE module
11b Wi-Fi module
13 main control module
15 position sensor module
15b GNSS receiving module
16 living body information detection sensor module
16A heart rate sensor
16B pulse rate sensor
17 ambient information acquisition sensor module
17A air pressure sensor
17B temperature sensor
18 state information detection sensor module
131 storage unit
131b transmission format pattern memory region
131c sensor data storage region
132 control unit
132f sensor information capture section
132g initial time capture format creation section
132i internal timer
132j initial time adjustment section
132k association section
132s position data calculation section
AS1 GNSS satellite
SPi athlete
SPai soccer player

The invention claimed is:

1. A moving body information detection terminal mounted on a moving body, comprising:
a communication module;
a position sensor module that receives global navigation satellite system (GNSS) data sent from a GNSS satellite and extracts, from the GNSS data, Raw data for obtaining position data;
an internal timer that outputs a system time no more than output timing of the position data synchronized with the Raw data;
a moving body situation detection sensor module comprising a variety of sensors that detect various pieces of information regarding the moving body at intrinsic pieces of timing and output the detected pieces of information as moving body situation detection data;
a storage region where the moving body situation detection data of the variety of sensors are stored;
a unit that overwrites the moving body situation detection data to a predetermined memory region of the storage region every fixed time, the moving body situation detection data being sent from the variety of sensors;
a unit that calculates the position data on the basis of the Raw data; and
a unit that defines the system time and the position data as header information, creates moving body information so that the moving body situation detection data stored in the memory region at a present time point is associated with the header information, and causes the communication module to transmit the created moving body information to an external device.

2. The moving body information detection terminal according to claim 1,
wherein, upon receiving, through the communication module, a request signal sent from the external device and requesting the moving body information, the unit that creates the moving body information and causes the communication module to transmit the created moving body information to the external device extracts, from the memory region, the moving body situation detection data corresponding to the request signal, and associates the extracted moving body situation detection data with the header information.

3. The moving body information detection terminal according to claim 2, further comprising:
a copy region;
a copy section that copies the moving body information on the copy region; and
a resending section that, when the request signal indicates resending, reads the moving body information corresponding to the request signal from the copy region, and transmits the moving body information to the external device.

4. The moving body information detection terminal according to claim 2, further comprising:
a pattern memory region; and
a unit that creates a transmission form comprising format regions equivalent to a number corresponding to the variety of sensors in the pattern memory region, the format regions storing therein the moving body situation detection data, wherein the unit that creates the moving body information and causes the communication module to transmit the created moving body information to the external device forms the moving body information only of the moving body situation detection data stored in the format regions of the transmission form.

5. The moving body information detection terminal according to claim 1, further comprising:

a reference position providing station that obtains correction data that is a difference of the position data from a reference position; and a correction section that corrects the position data based on the correction data sent from the reference position providing station every time when the position data is obtained.

6. The moving body information detection terminal according to claim 1, wherein the moving body situation detection sensor module comprises a state information detection sensor module that detects an attitude, acceleration and direction of the moving body.

7. The moving body information detection terminal according to claim 1,
wherein the moving body is a living body, and the moving body situation detection sensor module comprises a living body information detection sensor module that detects living body information of the living body.

8. The moving body information detection terminal according to claim 1, wherein the moving body situation detection sensor module comprises an ambient information acquisition sensor module that acquires environment information around the moving body.

9. The moving body information detection terminal according to claim 1, wherein the system time synchronized with the Raw data is included in the header information.

10. The moving body information detection terminal according to claim 1, wherein the association of the moving body situation detection data with the position data further causes association with the system time.

11. The moving body information detection terminal according to claim 1, wherein the communication module, the position sensor module, the moving body situation detection sensor module and the internal timer are integrated on a base.

* * * * *